US009216233B2

(12) United States Patent
Ota et al.

(10) Patent No.: US 9,216,233 B2
(45) Date of Patent: Dec. 22, 2015

(54) APPARATUS AND METHOD FOR CAPTURE AND INACTIVATION OF MICROBES AND VIRUSES

(71) Applicants: Koji Ota, Chiyoda-ku (JP); Yasutaka Inanaga, Chiyoda-ku (JP); Akira Morikawa, Chiyoda-ku (JP); Takahiro Sakai, Chiyoda-ku (JP)

(72) Inventors: Koji Ota, Chiyoda-ku (JP); Yasutaka Inanaga, Chiyoda-ku (JP); Akira Morikawa, Chiyoda-ku (JP); Takahiro Sakai, Chiyoda-ku (JP)

(73) Assignee: Mitsubishi Electric Corporation, Chiyoda-ku (JP)

( * ) Notice: Subject to any disclaimer, the term of this patent is extended or adjusted under 35 U.S.C. 154(b) by 56 days.

(21) Appl. No.: 14/241,612

(22) PCT Filed: Oct. 18, 2012

(86) PCT No.: PCT/JP2012/076953

§ 371 (c)(1),
(2) Date: Feb. 27, 2014

(87) PCT Pub. No.: WO2013/065497

PCT Pub. Date: May 10, 2013

(65) Prior Publication Data

US 2014/0205495 A1 Jul. 24, 2014

(30) Foreign Application Priority Data

Nov. 2, 2011 (JP) ................................ 2011-241636
Mar. 29, 2012 (WO) .................. PCT/JP2012/002184

(51) Int. Cl.
*A61L 9/00* (2006.01)
*A62B 7/08* (2006.01)

(Continued)

(52) U.S. Cl.
CPC ... *A61L 9/16* (2013.01); *A61L 9/22* (2013.01); *B03C 3/017* (2013.01); *B03C 3/09* (2013.01);

(Continued)

(58) Field of Classification Search
CPC ............. B03C 3/00; A61L 9/014; A61L 9/03; B01D 53/02
USPC .......... 422/4-5, 121, 186.04; 55/318; 95/2, 7, 95/57, 79; 96/3, 15, 24, 55, 60, 108
See application file for complete search history.

(56) References Cited

U.S. PATENT DOCUMENTS 6,245,126 B1 6/2001 Feldman et al.
2004/0121402 A1* 6/2004 Harper et al. .................. 435/7.1

(Continued)

FOREIGN PATENT DOCUMENTS

CN 101695683 A 4/2010
EP 2 578 243 A1 4/2013

(Continued)

OTHER PUBLICATIONS

Combined Chinese Office Action and Search Report issued Mar. 24, 2015 in Application Patent No. 201280042878.0 (with English language translation and English translation of categories of cited documents).

(Continued)

*Primary Examiner* — Monzer R Chorbaji
(74) *Attorney, Agent, or Firm* — Oblon, McClelland, Maier & Neustadt, L.L.P.

(57) ABSTRACT

An apparatus 100 includes an air path housing 10, a charging-unit high-voltage electrode 2 to charge airborne microorganisms introduced in the air path housing 10, a charging-unit ground electrode 3 disposed so as to face the charging-unit high-voltage electrode 2, a hydrophilic filter 6 to capture the airborne microorganisms charged by the charging-unit high-voltage electrode 2, a capturing/inactivating-unit high-voltage electrode 5 to polarize the hydrophilic filter 6, and a capturing/inactivating-unit ground electrode 7 disposed so as to face the capturing/inactivating-unit high-voltage electrode 5.

10 Claims, 20 Drawing Sheets

(51) Int. Cl.

| | |
|---|---|
| ***B01J 19/08*** | (2006.01) |
| ***B01D 50/00*** | (2006.01) |
| ***B03C 3/36*** | (2006.01) |
| ***B03C 1/00*** | (2006.01) |
| ***A61L 9/16*** | (2006.01) |
| ***A61L 9/22*** | (2006.01) |
| ***F24F 3/16*** | (2006.01) |
| ***B03C 3/34*** | (2006.01) |
| ***B03C 3/017*** | (2006.01) |
| ***B03C 3/09*** | (2006.01) |
| ***B03C 3/12*** | (2006.01) |
| ***B03C 3/38*** | (2006.01) |
| ***B03C 3/41*** | (2006.01) |
| ***B03C 3/47*** | (2006.01) |

(52) U.S. Cl.

CPC ... *B03C 3/12* (2013.01); *B03C 3/34* (2013.01); *B03C 3/368* (2013.01); *B03C 3/38* (2013.01); *B03C 3/41* (2013.01); *B03C 3/47* (2013.01); *F24F 3/166* (2013.01); *A61L 2209/16* (2013.01); *B03C 2201/04* (2013.01); *F24F 2003/1617* (2013.01); *F24F 2003/1635* (2013.01); *F24F 2003/1653* (2013.01); *F24F 2003/1664* (2013.01)

(56) References Cited

U.S. PATENT DOCUMENTS

| | | | |
|---|---|---|---|
| 2005/0109204 | A1 | 5/2005 | Coppom et al. |
| 2006/0180023 | A1 | 8/2006 | Coppom et al. |
| 2007/0137480 | A1 | 6/2007 | Bergeron et al. |
| 2013/0071298 | A1 | 3/2013 | Tanimura et al. |

FOREIGN PATENT DOCUMENTS

| | | | |
|---|---|---|---|
| JP | 1 249145 | | 10/1989 |
| JP | 2 66248 | | 5/1990 |
| JP | 4 29765 | | 1/1992 |
| JP | 7 256140 | | 10/1995 |
| JP | 11 188214 | | 7/1999 |
| JP | 11 262611 | | 9/1999 |
| JP | 2005 304821 | | 11/2005 |
| JP | 2006-43550 | A | 2/2006 |
| JP | 2006029664 | | 2/2006 |
| JP | 2007 512131 | | 5/2007 |
| JP | 2008 221077 | | 9/2008 |
| WO | WO 2005/021160 | A1 | 3/2005 |
| WO | WO 2011/152016 | A1 | 12/2011 |

OTHER PUBLICATIONS

International Search Report Issued Feb. 5, 2013 in PCT/JP12/076953 Filed Oct. 18, 2012.

Office Action issued Jan. 6, 2015 in Japanese Patent Application No. 2013-541700 (with English language translation).

European Supplementary Search Report issued Oct. 8, 2015 in Application No. 12845939.3-1803/2774628 PCT/JP2012076953, pp. 12.

* cited by examiner

F I G. 1
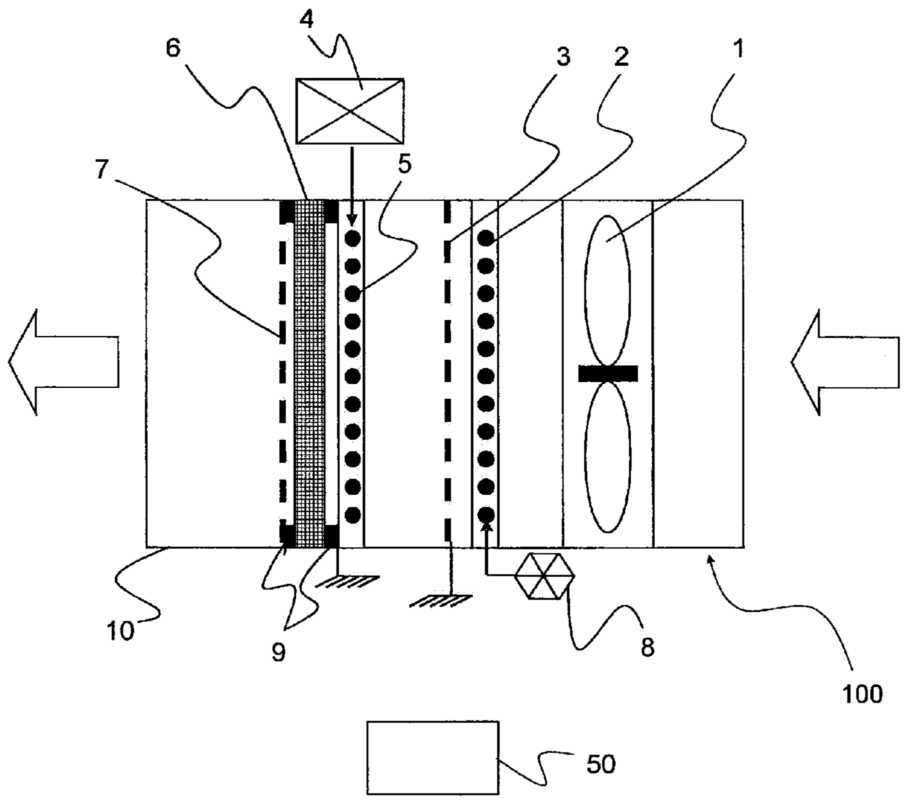

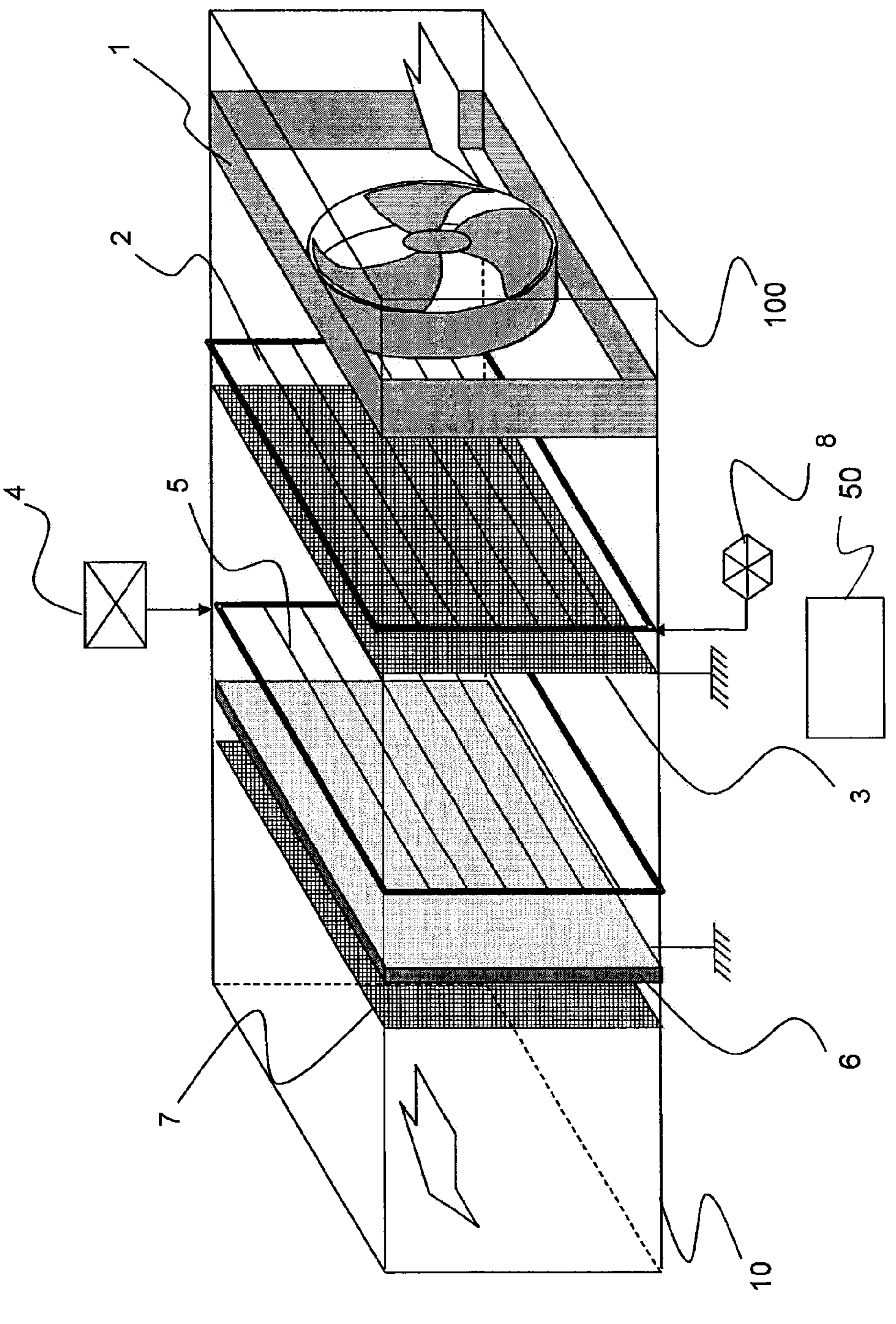
F I G. 2

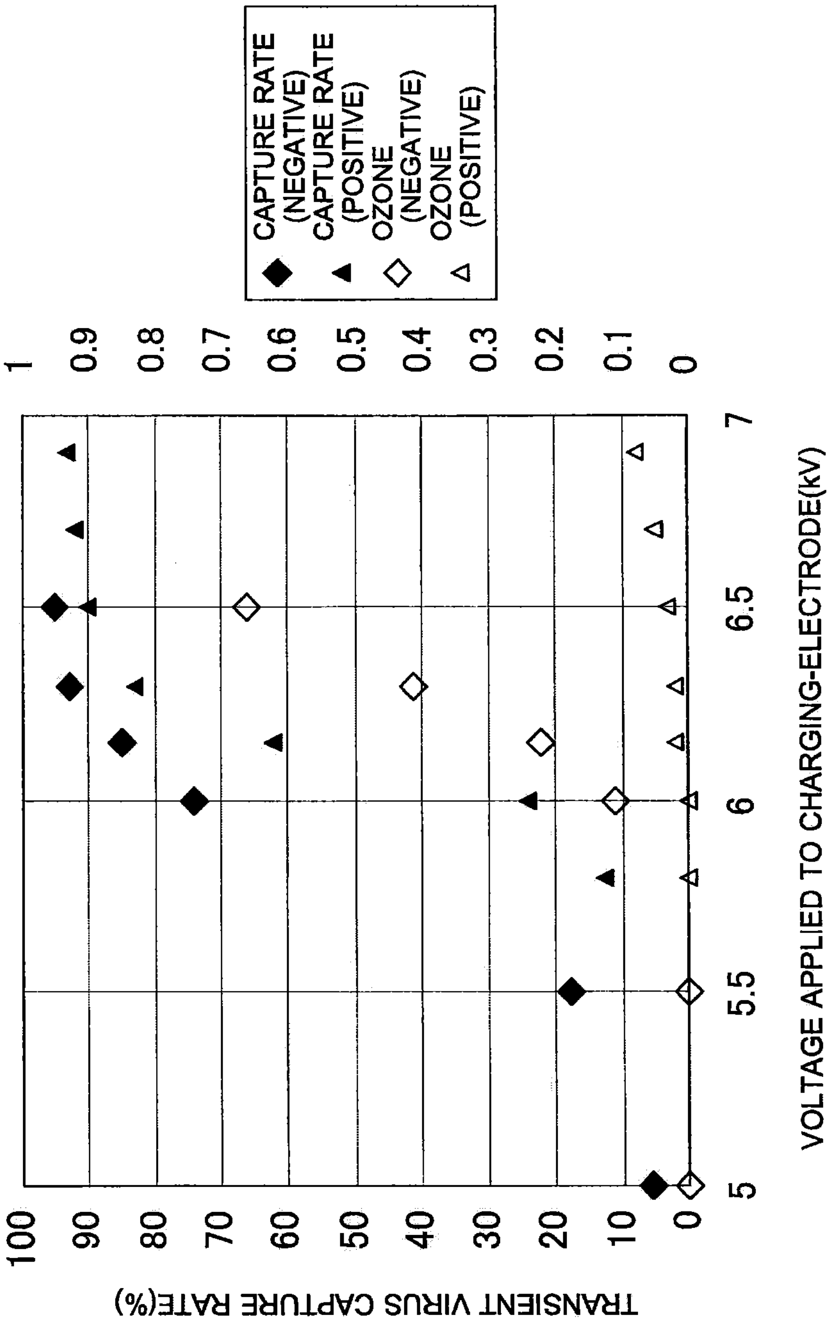
F I G. 6

F I G. 7
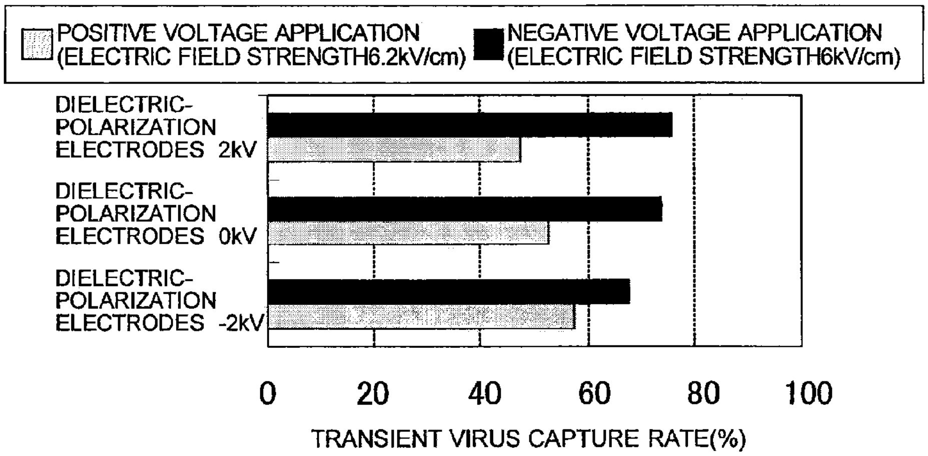
F I G. 8
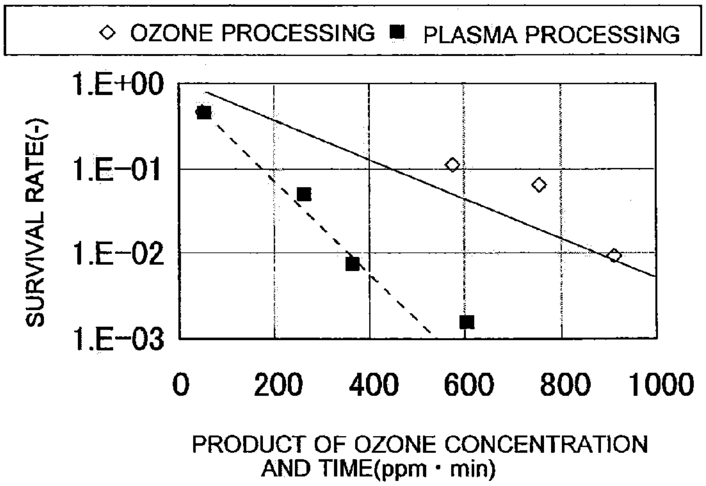

F I G. 1 5
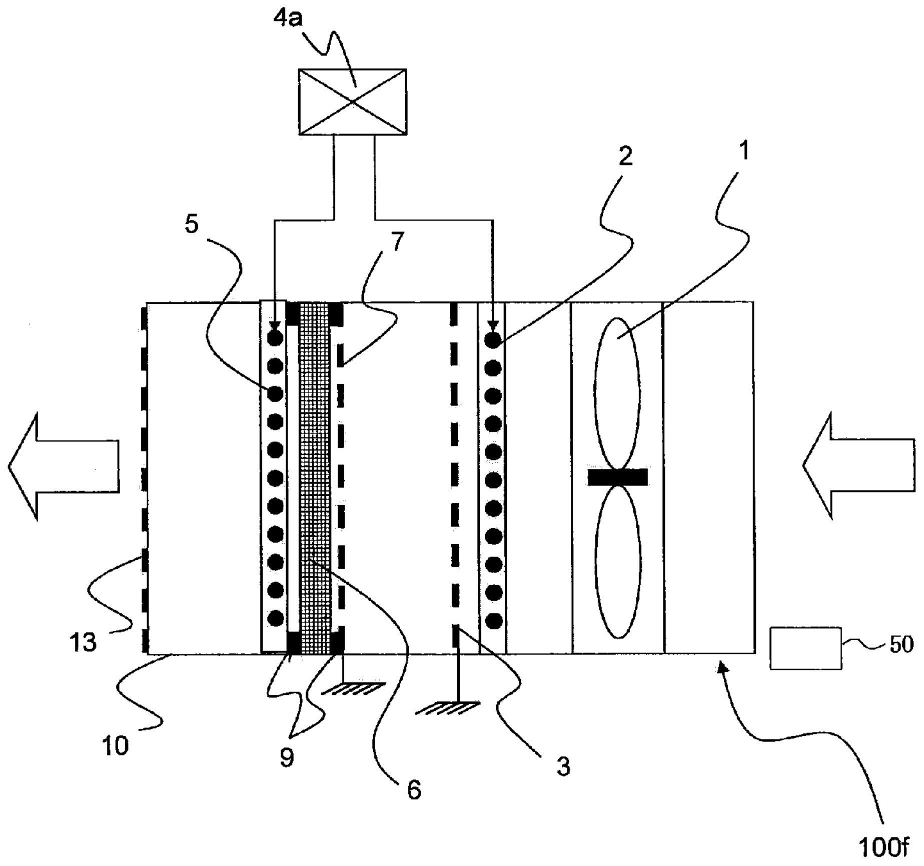

F I G. 1 9
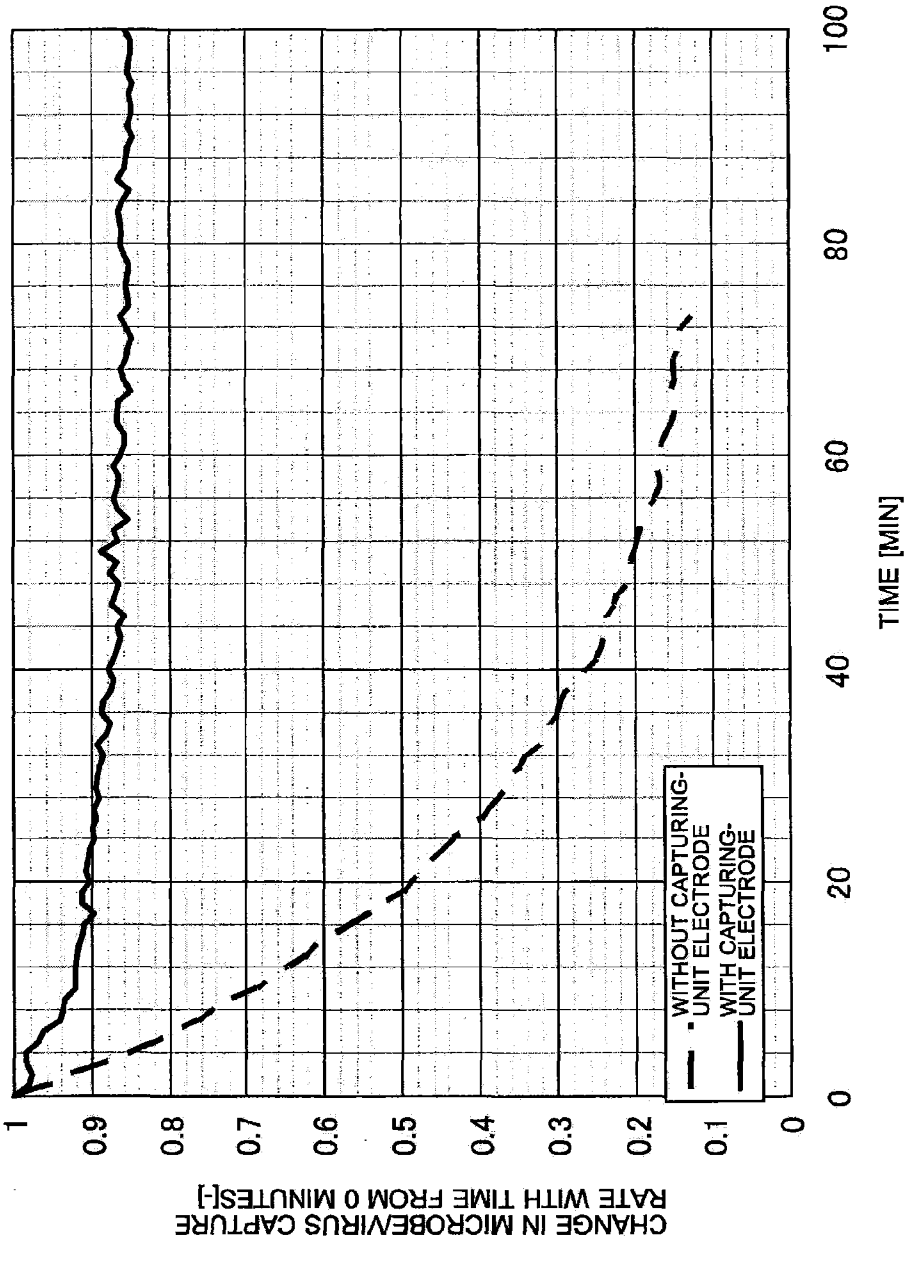

APPARATUS AND METHOD FOR CAPTURE AND INACTIVATION OF MICROBES AND VIRUSES

TECHNICAL FIELD

The present invention relates to an apparatus and method for capture and inactivation of microbes and viruses, the apparatus and method being capable of capturing and inactivating a microbe and/or a virus suspended in a space.

BACKGROUND ART

There have been airborne microbe/virus removal apparatuses for removing microbes and viruses suspended in a space. Such an airborne microbe/virus removal apparatus is disclosed which includes a corona charging unit, a high-voltage electrode, a filter, and an electrode in contact with the filter arranged in that order from a windward side to cancel out the effect of charge accumulation during operation so that high removal performance can be provided throughout the entire apparatus with a long life duration (refer to Patent Literature 1, for example).

Another airborne microbe/virus removal apparatus is disclosed which includes a pre-filter, a charging unit, a photocatalytic filter, an ultraviolet lamp, a virus capture filter, and an electrostatic filter arranged in that order from a windward side to enable functions of capturing and inactivating pathogenic viruses, such as an influenza virus, to be maintained for a long time (refer to Patent Literature 2, for example).

CITATION LIST

Patent Literature

Patent Literature 1: Japanese Unexamined Patent Application Publication (Translation of PCT application) No. 2007-512131 (p. 7, l. 17 to p. 10, l. 30, FIG. 1, for example)

Patent Literature 2: Japanese Unexamined Patent Application Publication No. 11-188214 (p. 7, l. 41 to p. 8, l. 51, FIG. 1, for example)

SUMMARY OF INVENTION

Technical Problem

In the airborne microbe/virus removal apparatus disclosed in Patent Literature 1, microbes and viruses deposited on the filter are again scattered upon application of an electric field. Disadvantageously, this lowers the advantage of capturing airborne microbes and airborne viruses in the airborne microbe/virus removal apparatus disclosed in Patent Literature 1. Furthermore, the airborne microbe/virus removal apparatus disclosed in Patent Literature 1 requires maintenance, such as filter cleaning, in order to prevent microbes and viruses captured by the filter from growing.

The airborne microbe/virus removal apparatus disclosed in Patent Literature 2 includes three filters, that is, the photocatalytic filter, a water drop type filter, and the electrostatic filter for airborne microbe/virus removal. Accordingly, this arrangement leads to an increase in pressure loss in the airborne microbe/virus removal apparatus disclosed in Patent Literature 2. Disadvantageously, for example, energy loss or noise may be caused.

The present invention has been made to overcome the above-described disadvantages and provides an apparatus and method for capture and inactivation of microbes and viruses, the apparatus and method being capable of stably removing a microbe and/or a virus and achieving a reduction in pressure loss.

Solution to Problem

The present invention provides a method for capture and inactivation of microbes and viruses, the method including a step of introducing airborne microorganisms into an air path housing, a charging step of charging the airborne microorganisms introduced in the air path housing, a filter capturing step of capturing the charged airborne microorganisms using a filter which has been polarized, and a step of inactivating the airborne microorganisms captured by the filter with plasma, wherein the step of inactivating the airborne microorganisms captured by the filter with plasma is started after the charging step and the filter capturing step.

The present invention provides a method for capture and inactivation of microbes and viruses, the method including a step of introducing airborne microorganisms into an air path housing, a step of producing a discharge between a first high-voltage application electrode and a first counter electrode disposed so as to face the first high-voltage application electrode in the air path housing to charge the airborne microorganisms introduced in the air path housing, a capturing step of capturing the charged airborne microorganisms using a filter charged in advance, and a step of inactivating the airborne microorganisms after the capturing step and sending air, wherein the steps are successively performed.

The present invention provides an apparatus for capture and inactivation of microbes and viruses, the apparatus including an air path housing, a first high-voltage application electrode to be supplied with a voltage to charge airborne microorganisms introduced in the air path housing, a first counter electrode disposed so as to face the first high-voltage application electrode, a filter to capture the airborne microorganisms charged by the first high-voltage application electrode, a second high-voltage application electrode to be supplied with a voltage to polarize the filter and inactivate the airborne microorganisms captured by the filter, a second counter electrode disposed so as to face the second high-voltage application electrode, and a power supply to supply a voltage to each of the first high-voltage application electrode and the second high-voltage application electrode. The filter has a hydrophilic surface. The filter is sandwiched between the second high-voltage electrode and the second counter electrode so as to be insulated from the electrodes.

Advantageous Effects of Invention

The apparatus and methods for capture and inactivation of microbes and viruses according to the present invention enable capture of microbes and viruses suspended in air with low pressure loss such that the microbes and viruses suspended in the air are charged and then captured, and enable inactivation of the captured viruses by discharge. Advantageously, a portion capturing the microbes and viruses can be kept in a clean state at all times.

BRIEF DESCRIPTION OF DRAWINGS

FIG. 1 is a sectional view illustrating a longitudinal section of a schematic configuration of an apparatus for capture and inactivation of microbes and viruses according to Embodiment 1 of the present invention.

FIG. 2 is a perspective view of the schematic configuration of the apparatus for capture and inactivation of microbes and viruses according to Embodiment 1 of the present invention.

FIG. 6 is a graph of the effect of the polarity of a voltage applied to the charging-unit high-voltage electrode of the apparatus for capture and inactivation of microbes and viruses according to Embodiment 1 of the present invention on the transient virus capture rate (%) and the concentration (ppm) of ozone generated, the effect having been examined.

FIG. 7 is a graph of the effect of the polarities of voltages applied to the charging-unit high-voltage electrode and the capturing/inactivating-unit high-voltage electrode of the apparatus for capture and inactivation of microbes and viruses according to Embodiment 1 of the present invention on the transient virus capture rate (%), the effect having been examined.

FIG. 8 is a graph of the comparison in virus survival rate between processing captured viruses with ozone gas alone and processing (plasma processing) captured viruses with other discharge products in addition to the ozone gas.

FIG. 15 is a sectional view illustrating a longitudinal section of a schematic configuration of an apparatus for capture and inactivation of microbes and viruses according to another modification of Embodiment 5 of the present invention.

FIG. 19 illustrates an example of a change in microbe/virus capture rate of a configuration with a capturing/inactivating-unit ground electrode 7 and that of a configuration without the capturing/inactivating-unit ground electrode 7.

DESCRIPTION OF EMBODIMENTS

Figure 3:
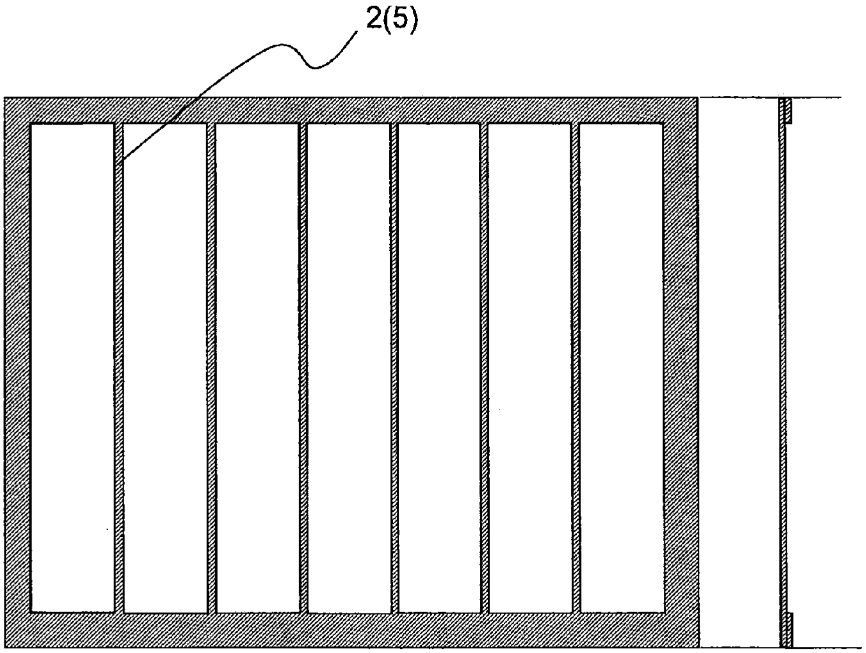
FIG. 3 is a schematic diagram illustrating a schematic exemplary configuration of a charging-unit high-voltage electrode and a capturing-and-inactivating-unit high-voltage electrode illustrated in FIG. 1.

Embodiments of the present invention will be described below with reference to the drawings.

Embodiment 1

FIG. 1 is a sectional view illustrating a longitudinal section of a schematic configuration of an apparatus (hereinafter, referred to as the "apparatus 100") for capture and inactivation of microbes and viruses according to Embodiment 1 of the present invention. FIG. 2 is a perspective view of the schematic configuration of the apparatus 100. The configuration and operation of the apparatus 100 will be described with reference to FIGS. 1 and 2. Note that the dimensional relationship among components in FIG. 1 and the following figures may be different from the actual one. Furthermore, the flow of air is indicated by arrows in FIGS. 1 and 2.

The apparatus 100 is configured to capture microbes and viruses (hereinafter, also referred to as "airborne microorganisms) suspended in a space and inactivate the captured airborne microorganisms. The apparatus 100 includes an air path housing 10, an air-sending device 1, a charging-unit high-voltage electrode (first high-voltage application electrode) 2, a charging-unit ground electrode (first counter electrode) 3, a capturing/inactivating-unit high-voltage electrode (second high-voltage application electrode) 5, a hydrophilic filter 6, and a capturing/inactivating-unit ground electrode (second counter electrode) 7 such that the components are arranged in the air path housing 10 in that order from a windward (upstream) side.

The air-sending device 1 is configured to introduce air into the air path housing 10. The charging-unit high-voltage electrode 2 is an electrode including many stretched conductive wires (made of tungsten, titanium, or stainless steel, or platinum clad wires (platinum-coated wires made of such a metal), or made of conductive resin) having a diameter in the range of, for example, approximately 0.05 mm to approximately 0.5 mm and is configured to be supplied with a high voltage from a high voltage power supply 8 connected to the electrode. The charging-unit ground electrode 3 is an electrode formed of, for example, metal mesh and is connected to ground. The charging-unit high-voltage electrode 2 and the charging-unit ground electrode 3 constitute a charging unit. The charging-unit high-voltage electrode 2 is spaced at a distance of 3 mm to 15 mm from the charging-unit ground electrode 3. A voltage of approximately 1 kV to approximately 15 kV is applied between the electrodes.

Although Embodiment 1 has been described on the assumption that the charging-unit ground electrode 3 functions as a first counter electrode, it is only required that a voltage be applied between the charging-unit high-voltage electrode 2 and the charging-unit ground electrode 3. The charging-unit ground electrode 3 does not necessarily have to be grounded. Furthermore, if the charging-unit high-voltage electrode 2 is formed of a conductive ribbon which has a rectangular or similar shaped cross-section having a sectional area of 0.1 mm×0.5 mm (and whose short sides correspond to a thickness in the range of 0.05 mm×0.5 mm and which has a width of approximately 0.3 mm to approximately 1 mm and which is made of tungsten, titanium, stainless steel, or conductive resin), the same advantages will be offered. In this case, more efficient charging is achieved in an arrangement in which a surface defined by short sides (0.1 mm) of the sectional area faces the charging-unit ground electrode 3. Furthermore, advantageously, the influence of disconnection due to electrode wear-out caused by sputtering during discharge can be reduced. Alternatively, as illustrated in FIG. 3, the charging-unit high-voltage electrode 2 may be formed as follows: a flat plate (having a thickness of 0.05 to 0.5 mm) is processed by etching, wire machining, laser machining, sheet metal stamping, or the like such that strip-shaped portions having a width of 0.3 to 1.0 mm are arranged, and the resultant workpiece is then reinforced such that edges of each opening are subjected to bending, such as hemming, or supported by an insulating material or the like in order to enable the electrode to have a sufficient strength.

The capturing/inactivating-unit high-voltage electrode 5 is an electrode including many stretched wires having a diameter in the range of, for example, approximately 0.1 mm to approximately 0.5 mm and is configured to be supplied with a high voltage from a high voltage power supply 4 connected to the electrode, the high voltage being in the range of approximately 1 kV to approximately 15 kV which may produce a corona discharge, or partial discharge. The capturing/inactivating-unit ground electrode 7 is an electrode formed of, for example, metal mesh and is connected to the ground.

Although Embodiment 1 has been described on the assumption that the capturing/inactivating-unit ground electrode 7 functions as a second counter electrode, it is only required that a voltage be applied between the capturing/inactivating-unit high-voltage electrode 5 and the capturing/inactivating-unit ground electrode 7. The capturing/inactivating-unit ground electrode 7 does not necessarily have to be grounded. Furthermore, if the capturing/inactivating-unit high-voltage electrode 5 is formed of a conductive ribbon which has a rectangular or similar shaped cross-section having a sectional area of 0.1 mm×0.5 mm (and which has a thickness of 0.1 mm), the same advantages will be offered. In this case, a surface defined by short sides (0.1 mm) of the sectional area may be allowed to face the charging-unit ground electrode 3. Alternatively, as illustrated in FIG. 3, the capturing/inactivating-unit high-voltage electrode 5 may be formed as follows: a flat plate (having a thickness of 0.05 to 0.5 mm) is processed by etching, wire machining, laser machining, sheet metal stamping, or the like such that strip-shaped portions having a width of 0.3 to 1.0 mm are arranged, and the resultant workpiece is then reinforced such that edges of each opening are subjected to bending, such as hemming, or supported by an insulating material or the like in order to enable the electrode to have a sufficient strength.

The hydrophilic filter 6 is sandwiched between the capturing/inactivating-unit high-voltage electrode 5 and the capturing/inactivating-unit ground electrode 7 paired with each other such that the filter is insulated by bushings 9 from the electrodes. The capturing/inactivating-unit high-voltage electrode 5, the hydrophilic filter 6, and the capturing/inactivating-unit ground electrode 7 constitute a capturing/inactivating unit. The high voltage power supply 4 is capable of supplying a voltage at one of at least two levels to the capturing/inactivating-unit high-voltage electrode 5.

FIG. 3 is a schematic diagram illustrating a schematic exemplary configuration of the charging-unit high-voltage electrode 2 and the capturing/inactivating-unit high-voltage electrode 5 illustrated in FIG. 1. Furthermore, as illustrated in FIG. 1, the apparatus 100 includes a controller 50 to control the apparatus 100 in a centralized manner. Apparatuses **100*a* to 100*j*, which will be described in Embodiments 2 to 9, each include the controller 50**.

In the above configuration, the hydrophilic filter 6, which is sandwiched between the capturing/inactivating-unit high-voltage electrode 5 and the capturing/inactivating-unit ground electrode 7 such that the filter is insulated from the electrodes and is grounded, is allowed to act as a dielectric, that is, to be polarized, such that an electrostatic field is produced on the surface of the hydrophilic filter 6. Accordingly, airborne microorganisms charged, or with charges applied by the charging unit composed of the charging-unit high-voltage electrode 2 and the charging-unit ground electrode 3 are attracted to the electric field produced on the surface of the hydrophilic filter 6, so that the airborne microorganisms come into collision with the hydrophilic filter 6. Furthermore, water suspended with the airborne microorganisms also collides with the hydrophilic filter 6, so that the water adheres to the hydrophilic filter 6. Consequently, microbes and viruses are prevented from being scattered again. The microbes and viruses captured by the hydrophilic filter 6 are inactivated by discharge products produced by discharge through the capturing/inactivating-unit high-voltage electrode 5.

As described above, the hydrophilic filter 6 is included in the capturing/inactivating unit in the apparatus 100. The hydrophilic filter 6 is polarized, so that charged airborne microorganisms can be efficiently guided to the hydrophilic filter 6 so as to collide with the surface of the hydrophilic filter 6 and the airborne microorganisms subjected to collision can be held with water. Advantageously, the apparatus 100 can capture airborne microorganisms with low pressure loss and can also prevent captured microbes and viruses from being scattered again.

Note that the hydrophilic filter 6 may be of any type capable of absorbing water (atomized water) subjected to collision. If the hydrophilic filter 6 is of a type that prevents formation of water droplets on the surface of the filter upon collision with water, the water held on the surface can be prevented from being scattered again. Thus, high capturing performance can be maintained.

An operation of the apparatus 100 will now be described.

Figure 4:
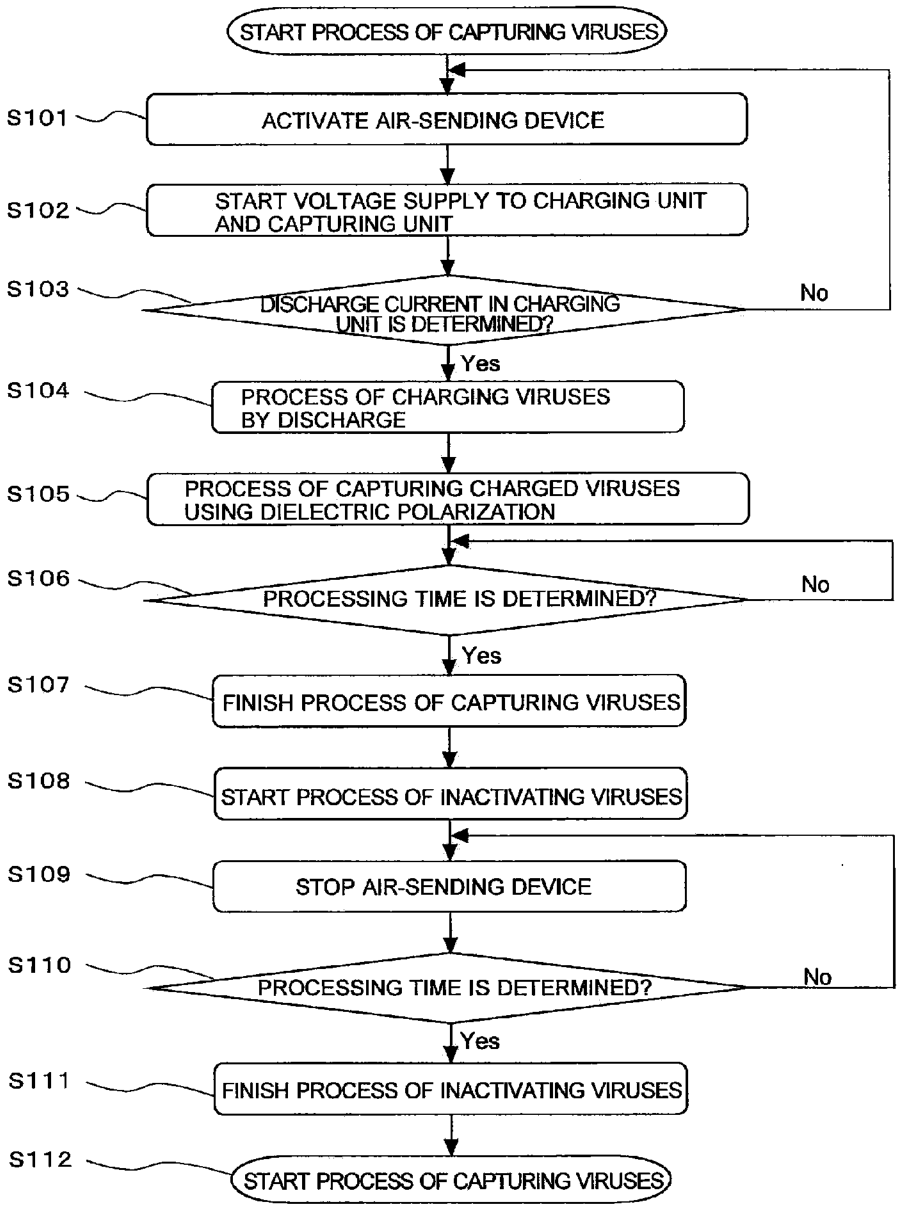
FIG. 4 is a flowchart illustrating the flow of a method for capture and inactivation of microbes and viruses, the method being executed by the apparatus for capture and inactivation of microbes and viruses according to Embodiment 1 of the present invention.

FIG. 4 is a flowchart illustrating the flow of a method for capture and inactivation of microbes and viruses, the method being executed by the apparatus 100. The apparatus 100 has a feature in that a specific portion is used for both capturing airborne microorganisms and inactivating the captured airborne microorganisms. Specifically, since the apparatus 100 is capable of executing a process of capturing microbes and viruses and a process of inactivating the captured microbes and viruses in a sequential order, the microbes and viruses can be removed with efficiency.

When the operation of the apparatus 100 is started, the air-sending device 1 is activated (step S101). The high voltage power supply 8 applies a high voltage to the charging-unit high-voltage electrode 2 and the high voltage power supply 4 applies a high voltage to the capturing/inactivating-unit high-voltage electrode 5 (step S102). Thus, a discharge is produced between the charging-unit high-voltage electrode 2 and the charging-unit ground electrode 3, so that discharge current flows into the charging-unit ground electrode 3. A current flowing into the charging-unit ground electrode 3 is measured by a current determining unit provided for, for example, a control board of the controller 50. The measured current is compared with a reference current previously set by the current determining unit (step S103). If there is no problem, the method proceeds to the next step (YES in step S103).

If the measured current is lower than the reference current, the voltage applied to the charging-unit high-voltage electrode 2 is raised. If the measured current is higher than the reference current, the voltage applied to the charging-unit high-voltage electrode 2 is lowered (step S104). Whether airborne microbes and viruses are efficiently charged at all times is determined in that manner (step S105). Upon start of the step (step S104) of charging microbes and viruses by the discharge and the step (step S105) of capturing the charged microbes and viruses using dielectric polarization, a timer is activated to measure processing time of these steps (step S106). The reference current may be manually set or may be previously stored as data in tabular form representing predetermined combinations in a storage unit. Furthermore, this reference value may be set in association with temperature and humidity. This facilitates the achievement of a predetermined charging rate.

When the processing time of these steps reaches reference time (YES in step S106), the application of the high voltage to the charging-unit high-voltage electrode 2 is stopped and the application of the high voltage to the capturing/inactivating-unit high-voltage electrode 5 is also stopped. After that, the series of steps (i.e., the process of capturing microbes and viruses) is finished (step S107).

The process of inactivating microbes and viruses is then started. The high voltage power supply 4 applies a high voltage to the capturing/inactivating-unit high-voltage electrode 5. Thus, a discharge is produced between the capturing/inactivating-unit high-voltage electrode 5 and the capturing/inactivating-unit ground electrode 7, so that discharge current flows into the capturing/inactivating-unit ground electrode 7. At this time, a current flowing into the capturing/inactivating-unit ground electrode 7 is measured by the current determining unit. The measured current is compared with a reference current previously set by the current determining unit. If there is no problem, the process of inactivating microbes and viruses is started (step S108).

In the process of inactivating microbes and viruses, if the measured current is lower than the reference current, the voltage applied to the capturing/inactivating-unit high-voltage electrode 5 is raised. If the measured current is higher than the reference current, the voltage applied to the capturing/inactivating-unit high-voltage electrode 5 is lowered. Whether the captured microbes and viruses are efficiently inactivated at all times is determined in this manner. Upon start of the process of inactivating microbes and viruses by the discharge (step S108), the air-sending device 1 is stopped (step S109) and the timer is activated to measure processing time of these steps (step S110).

When the processing time of these steps reaches reference time (YES in step S110), the application of the high voltage to the capturing/inactivating-unit high-voltage electrode 5 is stopped. The inactivating process is finished (step S111). After that, the process of charging and capturing microbes and viruses is again started (step S112). The above-described operation is repeated.

As described above, the apparatus 100 executes the step of charging airborne microorganisms (the step of allowing airborne microorganisms to be charged), the step of capturing the charged airborne microorganisms using the hydrophilic filter 6 which has been polarized, and the step of inactivating the airborne microorganisms captured by the hydrophilic filter 6 with plasma. Advantageously, the portion (hydrophilic filter 6) capturing the airborne microorganisms can be kept in a clean state at all times. Accordingly, the air in the space (such as a living space) where the apparatus 100 is installed can also be kept in a clean state at all times.

Low pressure loss and highly efficient capture due to charging by the corona discharge and the dielectric polarization of the hydrophilic filter 6, as a feature of the apparatus 100, will now be described. Table 1 illustrates the comparison in pressure loss (Pa) and transient virus capture rate (%) among the system of the apparatus 100 and related-art filtering systems.

TABLE 1

|  | System of This Application | HEPA Filter | Normal Filter |
| --- | --- | --- | --- |
| Pressure Loss [Pa] (at 1 m/s) | 10 | 150 | 10 |
| Transient Virus Capture Rate [%] | 95 | 99.9 | −5 |

Table 1 demonstrates that the system of the apparatus 100, that is, the dielectric polarization system using the hydrophilic filter 6 had a pressure loss of approximately 10 Pa, which is equal to that in the normal filter, in the flow of moving air at a linear velocity of 1 m/s. The transient virus capture rate at that time was approximately 95%, which is markedly higher than a transient virus capture rate of 5% in the normal filter. This may be attributed to the fact that static electricity enables viruses to collide with the filter with efficiency and the absorbability of water prevents the viruses subjected to collision from being scattered again. Furthermore, it was found that the transient virus capture rate in the HEPA filter (high efficiency particulate air filter) is higher than that in the system of the apparatus 100 but pressure loss in the filter is significantly higher than that in the system.

The above facts indicate that the use of the system of the apparatus 100 enables charging by the corona discharge and the dielectric polarization of the hydrophilic filter 6 to achieve the same level of transient virus capture rate as that in the HEPA filter while keeping the same level of pressure loss as that in the normal filter.

Figure 5:
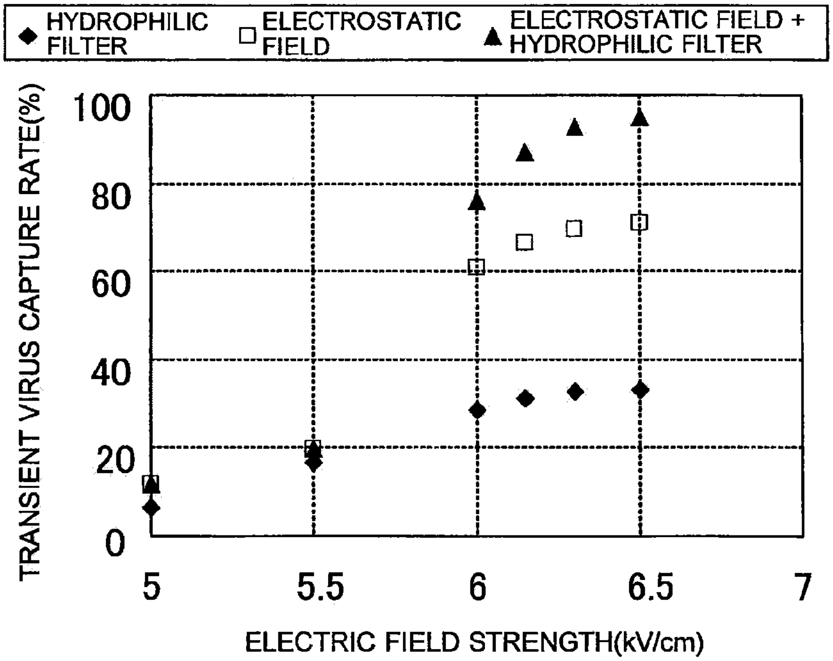
FIG. 5 is a graph of the relationship between the rate (%) of transient virus capture and the strength (kV/cm) of electric field between the capturing/inactivating-unit high-voltage electrode and a hydrophilic filter in the apparatus for capture and inactivation of microbes and viruses according to Embodiment 1 of the present invention, the relationship having been examined.

The effect of dielectric polarization of the hydrophilic filter 6, as the feature of the apparatus 100, on highly efficient virus capture will now be described. FIG. 5 is a graph of the relationship between the strength (kV/cm) of the electric field between the capturing/inactivating-unit high-voltage electrode 5 and the hydrophilic filter 6 and the transient virus capture rate (%), the relationship having been examined. In FIG. 5, the axis of abscissas indicates the electric field strength and the axis of ordinates indicates the transient virus capture rate.

Referring to FIG. 5, in the case where the hydrophilic filter 6 was not polarized, the transient virus capture rate was approximately 30% (indicated by solid black rectangles in FIG. 5) though viruses were charged by the corona discharge. In the case where a filter was polarized, the transient virus capture rate was increased to 70% (indicated by open rectangles in FIG. 5). Furthermore, in the case where the hydrophilic filter 6 was polarized, the transient virus capture rate was increased to 95% (indicated by solid black triangles in FIG. 5).

The above facts indicate that it is very important to polarize the hydrophilic filter 6. Thus, it is apparent that the hydrophilic filter 6 has to be polarized in order to achieve capture at or above 90%, at which it is generally determined that the advantage of removing microbes and viruses is offered.

FIG. 6 is a graph of the effect of the polarity of a voltage applied to the charging-unit high-voltage electrode 2 on the transient virus capture rate (%) and the concentration (ppm) of ozone generated, the effect having been examined. In FIG. 6, the axis of abscissas indicates the voltage (kV) applied at a distance of 10 mm between the charging-unit high-voltage electrode 2 and the charging-unit ground electrode 3, the left side of the axis of ordinates indicates the transient virus capture rate, and the right side thereof indicates the concentration of ozone generated.

Referring to FIG. 6, when a negative voltage was applied to the charging-unit high-voltage electrode 2, a transient virus capture rate of 95% was achieved with a lower applied voltage (indicated by solid black rectangles in FIG. 6). Furthermore, it was found that a positive voltage was preferably applied in order to achieve the concentration of ozone at or below 0.1 ppm at a transient virus capture rate of 95% (indicated by open triangles in FIG. 6).

The above facts indicate that, in the case where the apparatus 100 is adapted for use in air-conditioning equipment, it is preferable to charge viruses with positive voltage application to the electrode which enables maintaining a high transient virus capture rate while keeping a low amount of ozone generation.

FIG. 7 is a graph of the effect of the polarities of voltages applied to the charging-unit high-voltage electrode 2 and the capturing/inactivating-unit high-voltage electrode 5 on the transient virus capture rate (%), the effect having been examined. Referring to FIG. 7, in the case where a positive voltage was applied to the charging-unit high-voltage electrode 2, the transient virus capture rate was increased when the voltage applied to the capturing/inactivating-unit high-voltage electrode 5 was negative. In the case where a negative voltage was applied to the charging-unit high-voltage electrode 2, the transient virus capture rate was increased when the voltage applied to the capturing/inactivating-unit high-voltage electrode 5 was positive.

The above facts indicate that allowing the voltages applied to the charging-unit high-voltage electrode 2 and the capturing/inactivating-unit high-voltage electrode 5 to have opposite polarities increases the transient virus capture rate.

The above facts indicate that stable virus removal is achieved when a positive voltage is applied to the charging-unit high-voltage electrode 2 in a system in which the air velocity changes.

Inactivation of viruses captured with the hydrophilic filter 6 by the discharge will now be described, the inactivation being a second feature of the apparatus 100. Typically, viruses are not inactivated by merely applying voltages to electrodes such that the electrodes are polarized. The apparatus 100 is therefore designed to inactivate viruses using discharge products generated by a discharge produced by voltage application.

In investigating the electric field strengths and the polarities of applied voltages affected on the concentration (ppm) of ozone gas generated as one of discharge products, it can be seen from FIG. 6 that the concentration of ozone gas upon negative voltage application was higher than that upon positive voltage application at the same electric field strength. This fact indicates that negative voltage application is preferable in order to increase the efficiency of virus inactivation.

FIG. 8 is a graph of the comparison in virus survival rate between processing captured viruses with ozone gas alone and processing (plasma processing) captured viruses with other discharge products in addition to the ozone gas. In FIG. 8, the axis of abscissas indicates the product (ppm·min) of the concentration of ozone and time and the axis of ordinates indicates the survival rate (−). As illustrated in FIG. 8, even when ozone processing and plasma processing were performed at the same concentration of ozone, processing viruses in a plasma field achieved inactivation in a shorter time. This is probably because the viruses were inactivated by, for example, electrons, radicals, and ions in plasma, since captured viruses were exposed to the plasma field.

Accordingly, if the apparatus is designed such that the hydrophilic filter 6 for capturing viruses is placed in the plasma field, viruses can be inactivated in a short time. Advantageously, since the time required for inactivation can be reduced and the time for capturing airborne microorganisms can be lengthened, the apparatus 100 can remove the airborne microorganisms with higher efficiency.

Although a filter for removing dust in the air prior to charging airborne microorganisms is not described in Embodiment 1, it is needless to say that placing the filter for removing dust prior to the entrance of air into the charging unit for charging airborne microorganisms results in more efficient virus capture. Furthermore, although Embodiment 1 has been described with respect to the case where the air-sending device 1 is disposed on the windward side such that the air is forced to enter the virus capturing unit, it is needless to say that the same bactericidal effect can be obtained in an arrangement in which the air-sending device 1 is disposed on a leeward side so as to suck the air from the virus capturing unit.

Embodiment 2

Figure 9:
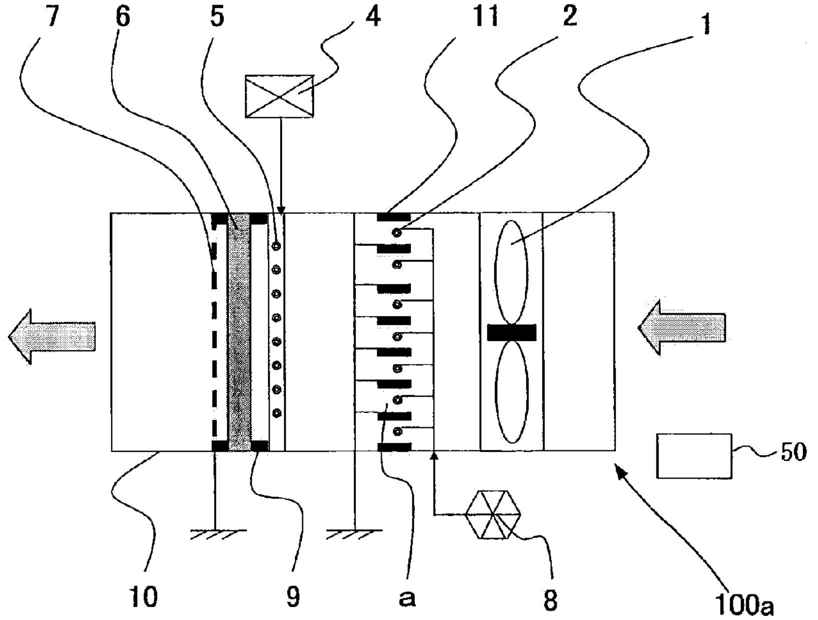
FIG. 9 is a sectional view illustrating a longitudinal section of a schematic configuration of an apparatus for capture and inactivation of microbes and viruses according to Embodiment 2 of the present invention.

FIG. 9 is a sectional view illustrating a longitudinal section of a schematic configuration of an apparatus (hereinafter, referred to as the "apparatus 100*a*") for capture and inactivation of microbes and viruses according to Embodiment 2 of the present invention. The configuration and operation of the apparatus 100*a* will be described with reference to FIG. 9. The difference between Embodiment 2 and Embodiment 1 will be mainly described. The same components as those in Embodiment 1 are designated by the same reference numerals. The flow of air is indicated by arrows in FIG. 9.

The apparatus 100*a* according to Embodiment 2 includes a charging unit placed leeward of the air-sending device 1, the charging unit including the charging-unit high-voltage electrode 2 and a charging-unit ground electrode 11. Specifically, the apparatus 100*a* differs from the apparatus 100 according to Embodiment 1 in the configuration of the charging unit. The charging-unit high-voltage electrode 2 is the electrode including many stretched conductive wires having a diameter in the range of, for example, approximately 0.1 mm to approximately 0.3 mm and is configured to be supplied with a high voltage from the high voltage power supply 8 connected to the electrode. The charging-unit ground electrode 11 is an electrode formed of, for example, a metal plate and is grounded.

This configuration offers the advantages described in Embodiment 1 and further enables a discharge space (space a in FIG. 9) defined by the charging-unit high-voltage electrode 2 and the charging-unit ground electrode 11 to be supplied with the whole amount of air introduced, thus efficiently charging airborne microorganisms. Accordingly, the apparatus 100*a* can maximize the microbe/virus capture rate of the capturing/inactivating unit including the capturing/inactivating-unit high-voltage electrode 5, the hydrophilic filter 6, and the capturing/inactivating-unit ground electrode 7. Furthermore, if the charging-unit high-voltage electrode 2 is formed of a conductive ribbon which has a rectangular or similar shaped cross-section having a sectional area of 0.1 mm×0.5 mm (and which has a thickness in the range of 0.1 mm to 0.3 mm and which is made of tungsten, titanium, stainless steel, or conductive resin), the same advantages will be offered. In this case, more efficient charging is achieved in an arrangement in which a surface defined by short sides (0.1 mm) of the sectional area faces the charging-unit ground electrode 11. Furthermore, advantageously, the influence of disconnection due to electrode wear-out caused by sputtering during discharge can be reduced.

Embodiment 3

Figure 10:
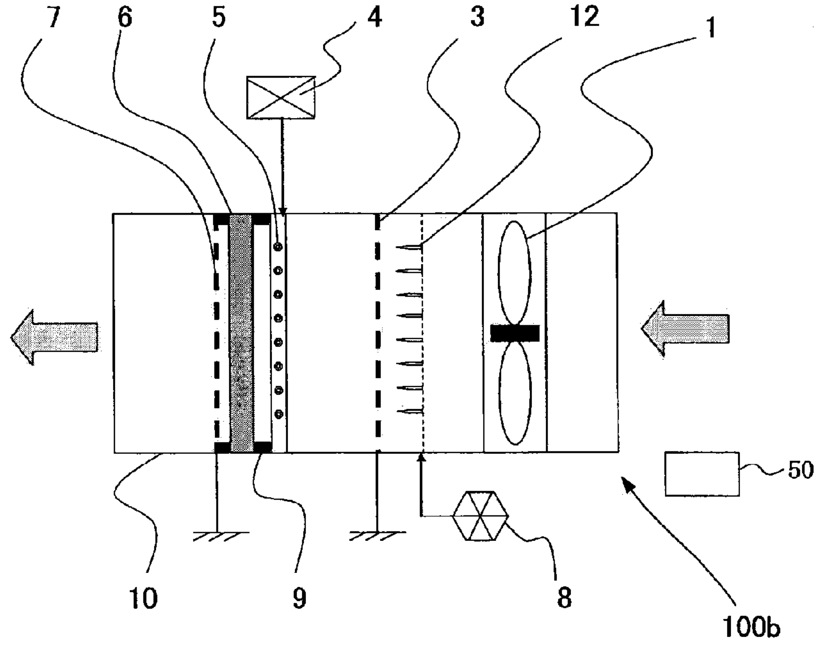
FIG. 10 is a sectional view illustrating a longitudinal section of a schematic configuration of an apparatus for capture and inactivation of microbes and viruses according to Embodiment 3 of the present invention.

FIG. 10 is a sectional view illustrating a longitudinal section of a schematic configuration of an apparatus (hereinafter, referred to as the "apparatus 100*b*") for capture and inactivation of microbes and viruses according to Embodiment 3 of the present invention. The configuration and operation of the apparatus 100*b* will be described with reference to FIG. 10. The difference between Embodiment 3 and Embodiments 1 and 2 will be mainly described. The same components as those in Embodiments 1 and 2 are designated by the same reference numerals. The flow of air is indicated by arrows in FIG. 10.

In the configuration in Embodiment 1, the charging-unit high-voltage electrode 2 formed of wires is disposed on the windward side and the charging-unit ground electrode 3 formed of metal mesh is disposed on the leeward side to charge microorganisms suspended in the air. According to Embodiment 3, a charging-unit high-voltage electrode 12 is an electrode including a plurality of conductive projections as illustrated in FIG. 10. For example, the projections may be attached to metal mesh or a plate, which permits the air to pass therethrough without pressure loss, by welding or the like to form the charging-unit high-voltage electrode 12 as illustrated in FIG. 10. According to a modification, a metal plate may be cut with a wire cutter or the like to provide projections, thus forming the charging-unit high-voltage electrode 12.

This configuration offers the advantages described in Embodiment 1 and further prevents the charging-unit high-voltage electrode 12 from being damaged due to an abnormal discharge caused by, for example, dust entering from the outside, so that stable discharge can be easily maintained.

Embodiment 4

Figure 11:
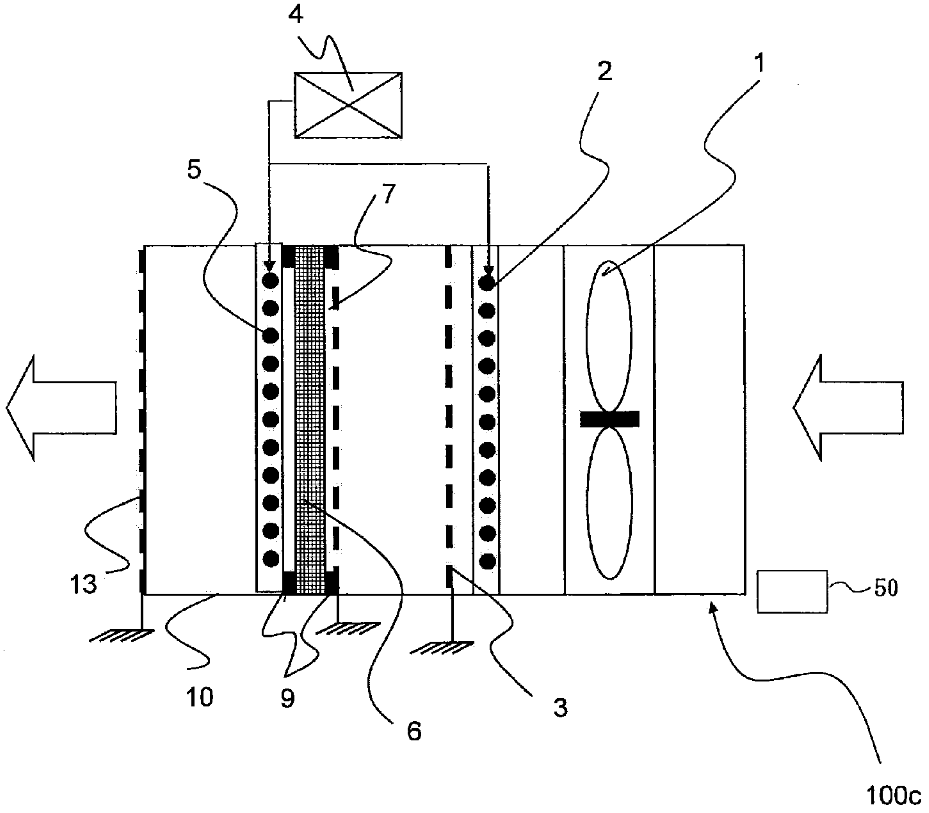
FIG. 11 is a sectional view illustrating a longitudinal section of a schematic configuration of an apparatus for capture and inactivation of microbes and viruses according to Embodiment 4 of the present invention.

FIG. 11 is a sectional view illustrating a longitudinal section of a schematic configuration of an apparatus (hereinafter, referred to as the "apparatus 100*c*") for capture and inactivation of microbes and viruses according to Embodiment 4 of the present invention. The configuration and operation of the apparatus 100*c* will be described with reference to FIG. 11. The difference between Embodiment 4 and Embodiments 1 to 3 will be mainly described. The same components as those in Embodiments 1 to 3 are designated by the same reference numerals. The flow of air is indicated by arrows in FIG. 11.

In the configuration in each of Embodiments 1 to 3, the two power supplies, that is, the high voltage power supply 8 for the charging-unit high-voltage electrode 2 and the high voltage power supply 4 for the capturing/inactivating-unit high-voltage electrode 5 are arranged. According to Embodiment 4, as illustrated in FIG. 11, the high voltage power supply 4 supplies a voltage to each of the charging-unit high-voltage electrode 2 and the capturing/inactivating-unit high-voltage electrode 5. The apparatus 100*c* further includes a safety guard 13 disposed at a leeward end thereof, the safety guard 13 being configured to prevent a user from accidentally inserting a user's finger into the apparatus 100*c*. The safety guard 13 is formed of, for example, conductive mesh having a mesh size in the range of approximately 1 mm to approximately 10 mm, this mesh size preventing the insertion of a human finger. The safety guard 13 is grounded and thus maintained at zero potential.

An operation of the apparatus 100*c* will now be described.

Figure 12:
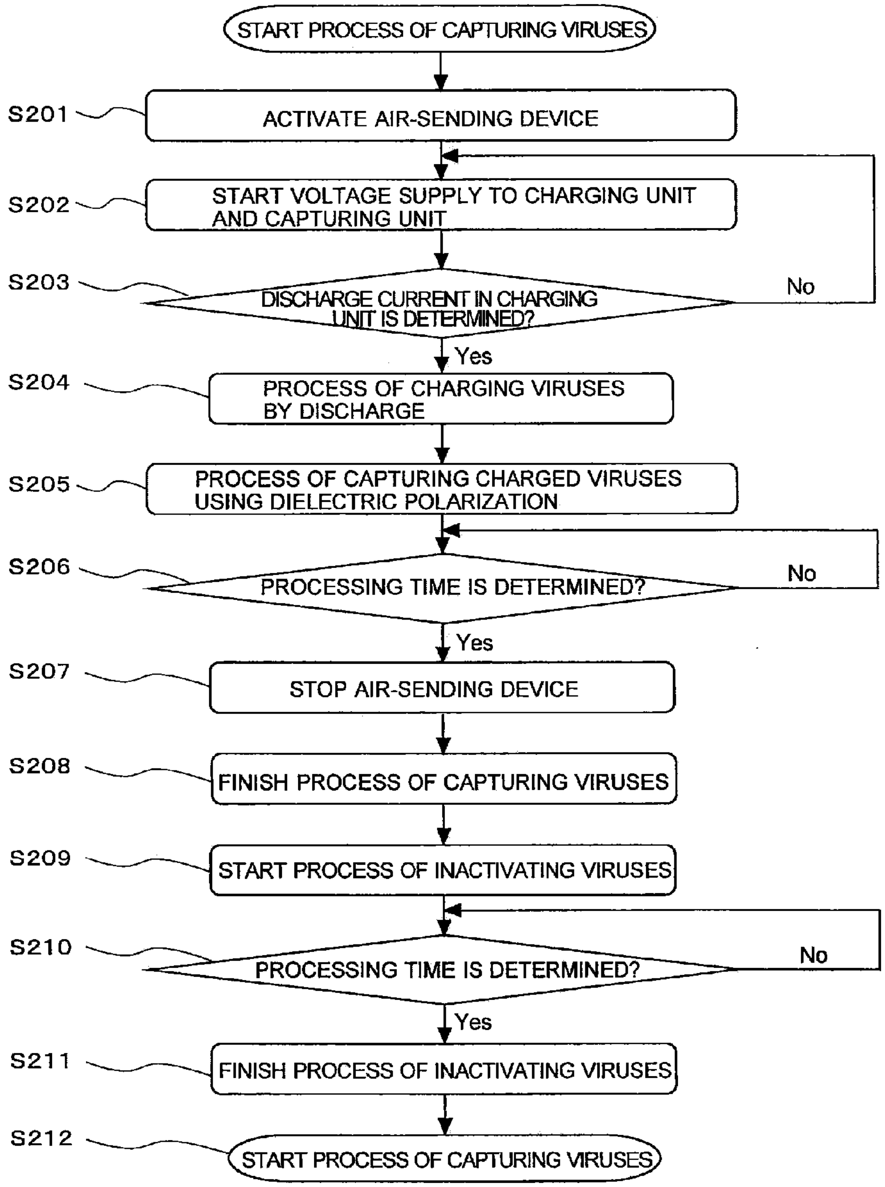
FIG. 12 is a flowchart illustrating the flow of a method for capture and inactivation of microbes and viruses, the method being executed by the apparatus for capture and inactivation of microbes and viruses according to Embodiment 4 of the present invention.

FIG. 12 is a flowchart illustrating the flow of a method for capture and inactivation of microbes and viruses, the method being executed by the apparatus 100*c*. The apparatus 100*c* has features in that a specific portion is used for both capturing airborne microorganisms and inactivating the captured airborne microorganisms and a same power supply is used for such processes. Specifically, since the apparatus 100*c* is capable of executing a process of capturing microbes and viruses and a process of inactivating the captured microbes and viruses in a sequential order, the microbes and viruses can be removed with efficiency.

When the operation of the apparatus 100*c* is started, the air-sending device 1 is activated (step S201). The high voltage power supply 4 applies a high voltage to the charging-unit high-voltage electrode 2 and also applies a high voltage to the capturing/inactivating-unit high-voltage electrode 5 (step S202). Thus, a discharge is produced between the charging-unit high-voltage electrode 2 and the charging-unit ground electrode 3, so that discharge current flows into the charging-unit ground electrode 3. A current flowing into the charging-unit ground electrode 3 is measured by a current determining unit provided for, for example, a control board of the controller 50. The measured current is compared with a reference current previously set by the current determining unit (step S203). If there is no problem, the method proceeds to the next step (YES in step S203).

If the measured current is lower than the reference current, the voltage applied to the charging-unit high-voltage electrode 2 is raised. If the measured current is higher than the reference current, the voltage applied to the charging-unit high-voltage electrode 2 is lowered (step S204). Whether airborne microbes and viruses are efficiently charged at all times is determined in that manner (step S205). Upon start of the step (step S204) of charging microbes and viruses by the discharge and the step (step S205) of capturing the charged microbes and viruses using dielectric polarization, a timer is activated to measure processing time of these steps (step S206).

When the processing time of these steps reaches reference time (YES in step S206), the application of the high voltage to the charging-unit high-voltage electrode 2 is stopped and the application of the high voltage to the capturing/inactivating-unit high-voltage electrode 5 is also stopped. The air-sending device 1 is then stopped (step S207). The series of steps (i.e., the process of capturing microbes and viruses) is finished (step S208).

The process of inactivating microbes and viruses is then started. The high voltage power supply 4 applies a high voltage to the capturing/inactivating-unit high-voltage electrode 5. Thus, a discharge is produced between the capturing/inactivating-unit high-voltage electrode 5 and the capturing/inactivating-unit ground electrode 7, so that discharge current flows into the capturing/inactivating-unit ground electrode 7. At this time, a current flowing into the capturing/inactivating-unit ground electrode 7 is measured by the current determining unit. The measured current is compared with a reference current previously set by the current determining unit. If there is no problem, the process of inactivating microbes and viruses is started (step S209).

In the process of inactivating microbes and viruses, if the measured current is lower than the reference current, the voltage applied to the capturing/inactivating-unit high-voltage electrode 5 is raised. If the measured current is higher than the reference current, the voltage applied to the capturing/inactivating-unit high-voltage electrode 5 is lowered. Whether the captured airborne microbes and viruses are efficiently inactivated at all times is determined in that manner. Upon start of the process of inactivating microbes and viruses by the discharge (step S209), the timer is activated to measure processing time of this process (step S210).

When the processing time of the process reaches reference time (YES in step S210), the application of the high voltage to the capturing/inactivating-unit high-voltage electrode 5 is stopped. The inactivating process is finished (step S211). After that, the process of charging and capturing microbes and viruses is again started (step S212). The above-described operation is repeated.

As described above, the apparatus 100*c* executes the step of charging airborne microorganisms (the step of allowing airborne microorganisms to be charged), the step of capturing the charged airborne microorganisms using the hydrophilic filter 6 which has been polarized, and the step of inactivating the airborne microorganisms captured by the hydrophilic filter 6 with plasma. Advantageously, the portion (hydrophilic filter 6) capturing the airborne microorganisms can be kept in a clean state at all times.

During the inactivating process, the air-sending device 1 is stopped and the discharge between the charging-unit high-voltage electrode 2 and the charging-unit ground electrode 3 is continued from the process of inactivating microbes and viruses. In this case, since the air-sending device 1 is stopped, the concentration of ozone in the capturing portion (hydrophilic filter 6) is raised. During inactivation in the combination use of ozone and plasma, as the concentration of ozone is higher, processing can be achieved in a shorter time.

In addition, the grounded safety guard 13 prevents the user from accidentally getting a high-voltage electrical shock. Furthermore, charged particles, such as ions, are neutralized by landing in the safety guard 13, thus preventing the charged particles from being emitted from the apparatus 100*c*. Accordingly, air in a space (such as a living space) where the apparatus 100*c* is installed can also be kept in a clean state at all times.

Embodiment 5

Figure 13:
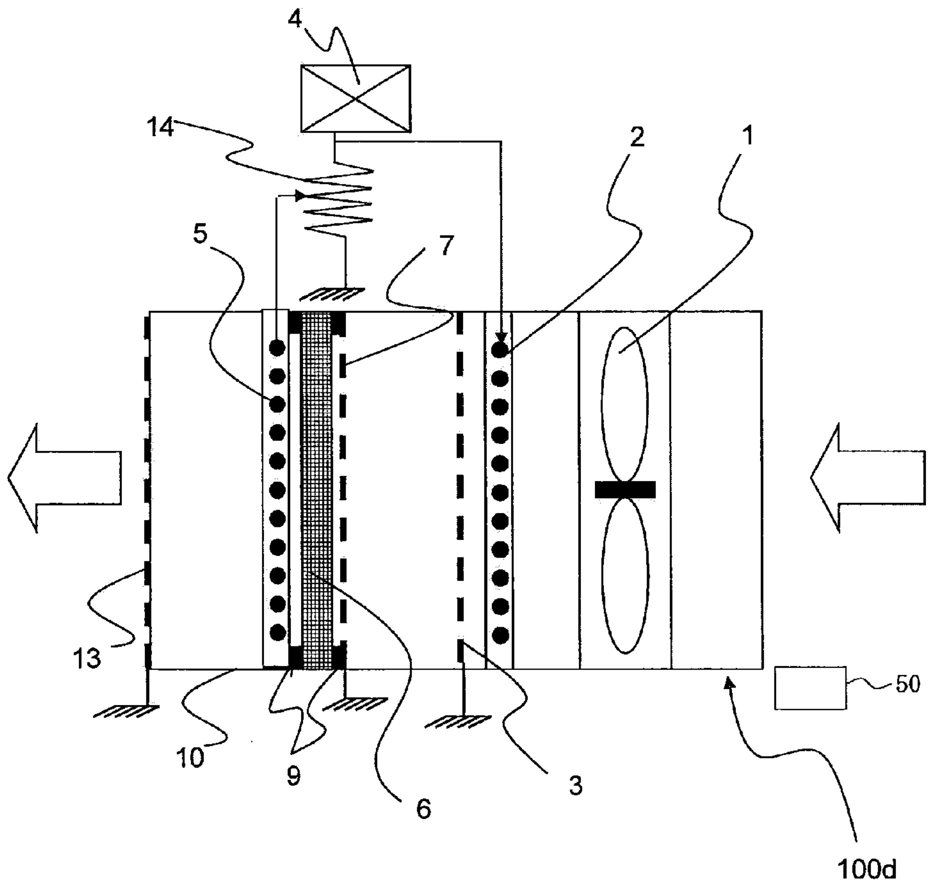
FIG. 13 is a sectional view illustrating a longitudinal section of a schematic configuration of an apparatus for capture and inactivation of microbes and viruses according to Embodiment 5 of the present invention.
Figure 14:
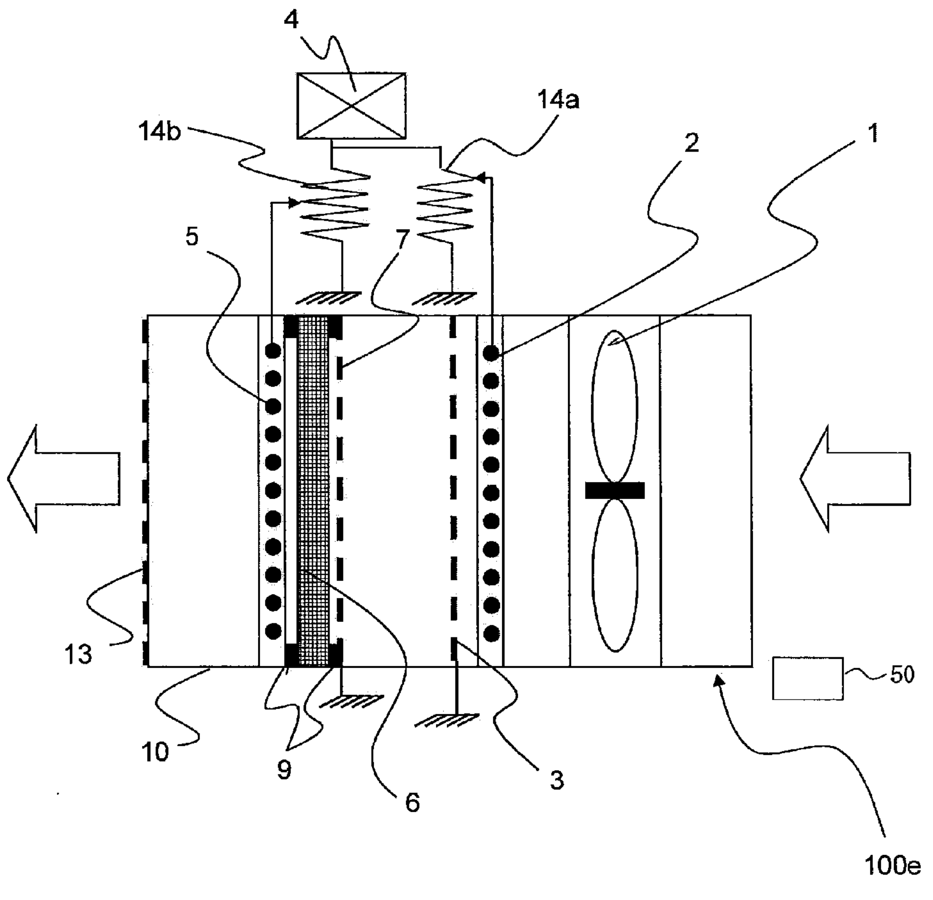
FIG. 14 is a sectional view illustrating a longitudinal section of a schematic configuration of an apparatus for capture and inactivation of microbes and viruses according to a modification of Embodiment 5 of the present invention.

FIG. 13 is a sectional view illustrating a schematic sectional configuration of an apparatus (hereinafter, referred to as the "apparatus 100*d*") for capture and inactivation of microbes and viruses according to Embodiment 5 of the present invention. FIG. 14 is a sectional view illustrating a schematic sectional configuration of a modification (hereinafter, referred to as an "apparatus 100*e*") of an apparatus 100*g*. FIG. 15 is a sectional view illustrating a schematic sectional configuration of a modification (hereinafter, referred to as an "apparatus 100*f*") of the apparatus 100*d*. The configurations and operations of the apparatuses 100*d* to 100*f* will be described with reference to FIGS. 13 to 15. The difference between Embodiment 5 and Embodiments 1 to 4 will be mainly described. The same components as those in Embodiments 1 to 4 are designated by the same reference numerals. Furthermore, the flow of air is indicated by arrows in FIGS. 13 to 15.

In Embodiment 4, as illustrated in FIG. 11, the high voltage power supply 4 supplies a voltage to each of the charging-unit high-voltage electrode 2 and the capturing/inactivating-unit high-voltage electrode 5. According to Embodiment 5, a voltage to be supplied to the capturing/inactivating-unit high-voltage electrode 5 can be regulated by a voltage regulator 14.

As described above, during capture of microbes and viruses, the high voltage power supply 4 applies a voltage to the charging-unit high-voltage electrode 2 to produce a discharge between the charging-unit high-voltage electrode 2 and the charging-unit ground electrode 3. At the same time, the high voltage power supply 4 applies a voltage to the capturing/inactivating-unit high-voltage electrode 5 to produce an electric field between the capturing/inactivating-unit high-voltage electrode 5 and the capturing/inactivating ground electrode 7, thus capturing microbes and viruses. In this case, if charging by the charging unit is insufficient, alternatively, if the distance between the capturing/inactivating-unit high-voltage electrode 5 and the hydrophilic filter 6 differs from a designed value, an abnormal discharge may be caused depending on conditions. In order to prevent the abnormal discharge, the voltage regulator 14 is provided for the apparatus 100*d*.

The voltage regulator 14 includes high-voltage resistors connected in series to divide a voltage in accordance with the resistance ratio and apply the resultant voltage to the capturing/inactivating-unit high-voltage electrode 5. Thus, different voltages can be applied to the charging-unit high-voltage electrode 2 and the capturing/inactivating-unit high-voltage electrode 5. Furthermore, the controller 50 may transmit a signal to the voltage regulator 14 so that a voltage different from that during capture can be applied to the capturing/inactivating-unit high-voltage electrode 5 during inactivation.

Although the voltage regulator 14 is connected to the capturing/inactivating-unit high-voltage electrode 5 in the apparatus 100*d*, the apparatus 100*e* may be configured such that a voltage regulator 14*a* is connected to the charging-unit high-voltage electrode 2 and a voltage regulator 14*b* is connected to the capturing/inactivating-unit high-voltage electrode 5, as illustrated in FIG. 14. Consequently, the voltages to be applied to the charging unit and the capturing/inactivating unit can be flexibly changed, so that a voltage can be set for each of the charging unit and the capturing/inactivating unit depending on environmental conditions under which microbes and viruses are removed.

Furthermore, the same advantages can be obtained in the use of a same power supply with at least two different output terminals, like a high voltage power supply 4*a* in the apparatus 100*f* illustrated in FIG. 15, to achieve supply of different voltages to the charging-unit high-voltage electrode 2 and the capturing/inactivating-unit high-voltage electrode 5.

As illustrated in FIGS. 13 to 15, air in respective spaces (such as living spaces) where the apparatuses 100*d* to 100*f* are installed can be kept in a clean state at all times.

Embodiment 6

Figure 16:
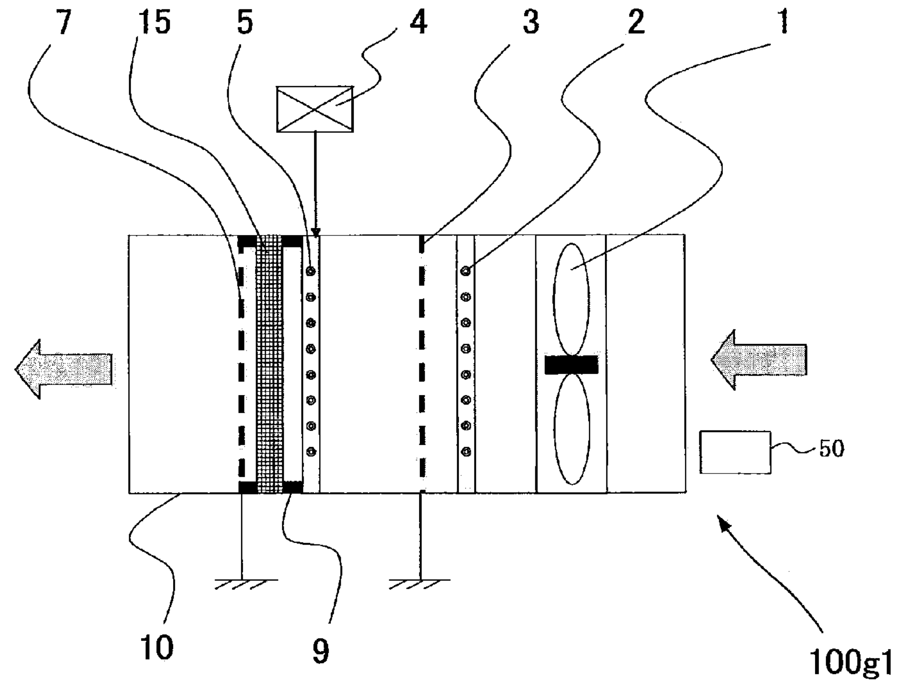
FIG. 16 is a sectional view illustrating a longitudinal section of a schematic configuration of an apparatus for capture and inactivation of microbes and viruses according to Embodiment 6 of the present invention.
Figure 17:
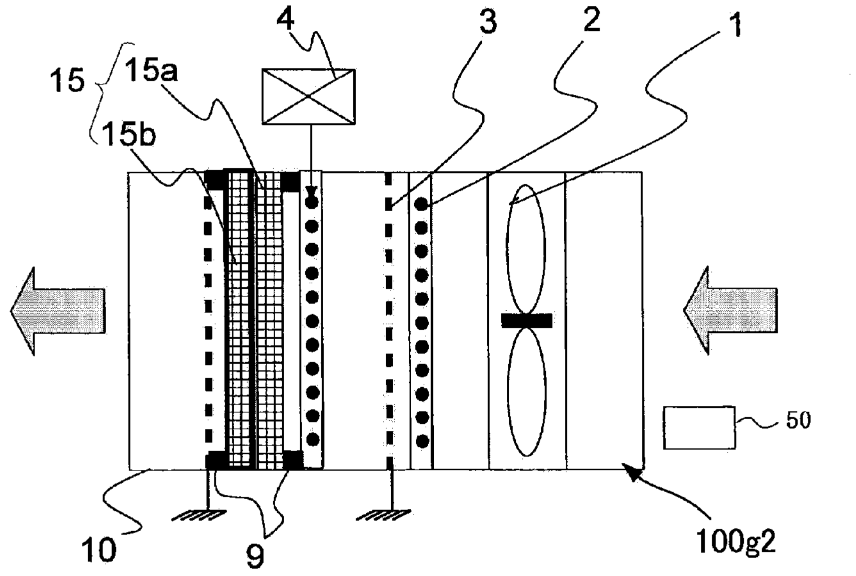
FIG. 17 is a sectional view illustrating a longitudinal section of a schematic configuration of an apparatus for capture and inactivation of microbes and viruses according to a modification of Embodiment 6 of the present invention.

FIG. 16 is a sectional view illustrating a longitudinal section of a schematic configuration of an apparatus (hereinafter, referred to as the "apparatus 100*g*1") for capture and inactivation of microbes and viruses according to Embodiment 6 of the present invention. FIG. 17 is a sectional view illustrating a longitudinal section of a schematic configuration of a modification (hereinafter, referred to as an "apparatus 100*g*2") of the apparatus 100*g*1. The configurations and operations of the apparatuses 100*g*1 and 100*g*2 will be described with reference to FIGS. 16 and 17. The difference between Embodiment 6 and Embodiments 1 to 5 will be mainly described. The same components as those in Embodiments 1 to 5 are designated by the same reference numerals. Furthermore, the flow of air is indicated by arrows in FIGS. 16 and 17.

Embodiment 6 relates to a modification of the capturing unit based on the configuration in Embodiment 1. Specifically, in each of Embodiments 1 to 5, the capturing unit includes the capturing/inactivating-unit high-voltage electrode 5, the hydrophilic filter 6, and the capturing/inactivating-unit ground electrode 7 such that the capturing/inactivating-unit high-voltage electrode 5 is connected to the high voltage power supply 4, the capturing/inactivating-unit ground electrode 7 is grounded, and the hydrophilic filter 6 is sandwiched between the paired electrodes to capture microorganisms suspended in the air. According to Embodiment 6, as illustrated in FIG. 16, a hydrophilic filter is a honeycomb structure (hereinafter, referred to as the "honeycomb 15") supporting a hydrophilic absorbent on its surface.

The honeycomb 15 is configured such that the hydrophilic absorbent is supported on the surface of the honeycomb made of, for example, metal (e.g., stainless steel or aluminum), ceramic, or paper. Examples of the hydrophilic absorbent include hydrophilic zeolite, which is effective. Any absorbent exhibiting high hygroscopicity may be used. The honeycomb 15 can be formed by immersing, for example, a metal honeycomb member into a slurry solution containing activated carbon, drying the resultant member, and then firing the member at a proper temperature.

This configuration offers the advantages described in Embodiment 1 and further prevents airborne microorganisms charged by the charging unit from being formed into droplets on the surface of the honeycomb 15 upon collision with the honeycomb 15 which has been polarized. Furthermore, the airborne microorganisms subjected to collision can be trapped in pores on the surface of the absorbent. Accordingly, an electric field produced around the honeycomb 15 prevents viruses and microbes from being scattered again and the viruses and microbes can be captured with high efficiency and be held as captured. Since the hydrophilic absorbent is used, odor components can also be captured.

As described above, the capturing unit including the capturing/inactivating-unit high-voltage electrode 5, the honeycomb 15, and the capturing/inactivating-unit ground electrode 7 achieves the advantage of capturing not only airborne microorganisms but also chemical substances, such as odor components, with high efficiency.

Although Embodiment 6 has been described with respect to the case where the honeycomb member made of metal or the like is coated with the hydrophilic absorbent, a catalytic substance, such as manganese dioxide ($MnO_2$), titanium dioxide ($TiO_2$), zinc oxide (ZnO), platinum (Pt), copper (Cu), or silver (Ag), may be supported on the surface of the absorbent. This enables the catalyst to be activated during plasma processing in the process of inactivating viruses and microbes with plasma or to transform discharge products into substances exhibiting higher activity. Consequently, viruses and microbes can be inactivated in a shorter time. Furthermore, chemical substances deposited on the honeycomb 15 can be decomposed and removed.

The honeycomb 15 may include two or more honeycombs (e.g., a hydrophilic honeycomb 15*a* and a catalyst-coated honeycomb 15*b*), as in the apparatus 100*g*2 illustrated in FIG. 17. In this case, preferably, the hydrophilic honeycomb 15*a* is placed close to the charging unit (on the upstream side) and the catalyst-coated honeycomb 15*b* is placed away from the charging unit (on the downstream side). In other words, it is only required that the honeycomb positioned closest to the charging unit be hydrophilic. The other honeycomb should not be particularly limited. The catalyst-coated honeycomb 15*b* is coated with, for example, an absorbent for absorbing an odor gas or a catalyst for decomposing and reducing the above-described odor components. Note that the catalyst-coated honeycomb 15*b* may be hydrophilic or hydrophobic in this configuration. Preferably, the catalyst-coated honeycomb 15*b* is coated with a hydrophilic absorbent and a hydrophobic absorbent in combination, because the number of gases which can be absorbed or decomposed is increased.

Since the honeycomb 15 enables the capturing unit to decompose discharge products (e.g., ozone) generated in the charging unit while capturing airborne microorganisms, the efficiency of charging airborne microorganisms by the charging unit can be enhanced. Accordingly, the apparatuses 100*g*1 and 100*g*2 maximize the efficiency of capturing airborne microorganisms by the capturing unit and further enhance the efficiency of removing viruses and microbes.

Embodiment 7

Figure 18:
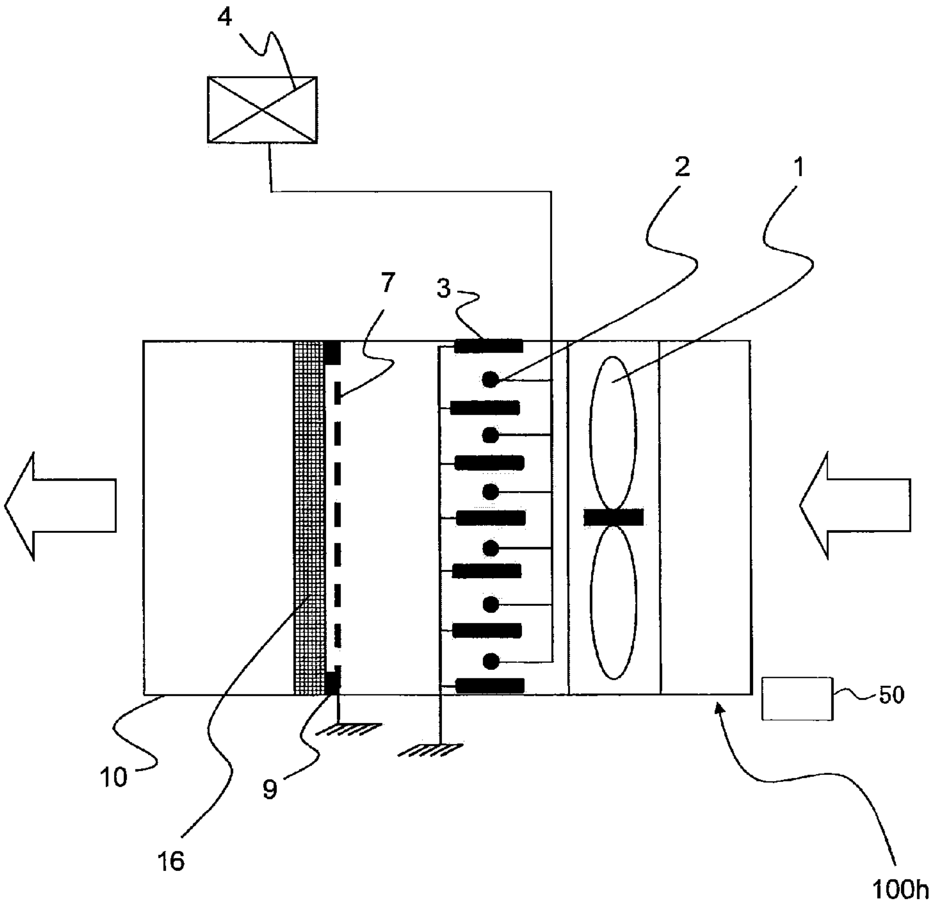
FIG. 18 is a sectional view illustrating a longitudinal section of a schematic configuration of an apparatus for capture and inactivation of microbes and viruses according to Embodiment 7 of the present invention.

FIG. 18 is a sectional view illustrating a longitudinal section of a schematic configuration of an apparatus (hereinafter, referred to as the "apparatus 100*h*") for capture and inactivation of microbes and viruses according to Embodiment 7 of the present invention. The configuration and operation of the apparatus 100*h* will be described with reference to FIG. 18. The difference between Embodiment 7 and Embodiments 1 to 6 will be mainly described. The same components as those in Embodiments 1 to 6 are designated by the same reference numerals. The flow of air is indicated by arrows in FIG. 18.

Embodiment 7 relates to a modification of the capturing unit based on the configuration in Embodiment 2. Specifically, in each of Embodiments 1 to 6, the capturing unit includes the capturing/inactivating-unit high-voltage electrode 5, the hydrophilic filter 6, and the capturing/inactivating-unit ground electrode 7 such that the capturing/inactivating-unit high-voltage electrode 5 is connected to the high voltage power supply 4, the capturing/inactivating-unit ground electrode 7 is grounded, and the hydrophilic filter 6 is sandwiched between the paired electrodes to capture microorganisms suspended in the air. According to Embodiment 6, as illustrated in FIG. 18, the capturing unit includes an electrostatic filter 16 and the capturing/inactivating-unit ground electrode 7 disposed upstream of the filter with an insulator (bushing 9) therebetween.

In the apparatus 100*h*, the electrostatic filter 16 charged in advance is used. Accordingly, an external electrode is not needed, thus simplifying the configuration. FIG. 19 illustrates an example of a change in microbe/virus capture rate of the configuration with the capturing/inactivating-unit ground electrode 7 and that without the capturing/inactivating-unit ground electrode 7. In FIG. 19, the axis of abscissas indicates the time elapsed from the start of capturing and the axis of ordinates indicates the rate of change in microbe/virus capture rate, the change rate being 1 when the elapsed time is 0 minutes.

As described above, the microbe/virus capture rate decreased with time in the configuration with no electrode having a ground potential disposed upstream of the electrostatic filter 16. On the other hand, the microbe/virus capture rate could be kept at high levels in the configuration with the capturing/inactivating-unit ground electrode 7, disposed upstream of the electrostatic filter 16, having the ground potential. Ions generated by the charting unit are deposited on the electrostatic filter 16, so that the deposited ions produce an electric field opposite to that produced by the charging-unit electrodes (the charging-unit high-voltage electrode 2, the charging-unit ground electrode 3). The electric field opposite to that produced by the charging-unit electrodes functions to reduce the charging efficiency of the charging unit.

The capturing/inactivating-unit ground electrode 7 neutralizes the ions generated by the charging-unit electrodes, thus preventing accumulation of charges on the electrostatic filter 16 and maintaining the microbe/virus capture rate at a high level. Furthermore, microbes and viruses captured by the electrostatic filter 16 are exposed to ozone produced between the charging-unit high-voltage electrode 2 and the charging-unit ground electrode 3 for a long time, so that the microbes and viruses can be inactivated. Additionally, if the electrostatic filter 16 is in honeycomb form (or form having many holes, i.e., form having partitions), it can be configured with low pressure loss in a manner similar to Embodiment 6. Furthermore, the electrostatic filter 16 may be coated with an absorbent or catalyst. Alternatively, a deodorant catalyst or a $MnO_2$ catalyst to decompose generated ozone may be disposed leeward of the electrostatic filter 16. Consequently, the same advantages as those of Embodiment 6 can be offered.

Accordingly, the air in a space (such as a living space) where the apparatus 100*h* is installed can be similarly kept in a clean state at all times. It is preferred that the electrostatic filter 16 have permanent static electricity.

Embodiment 8

Figure 20:
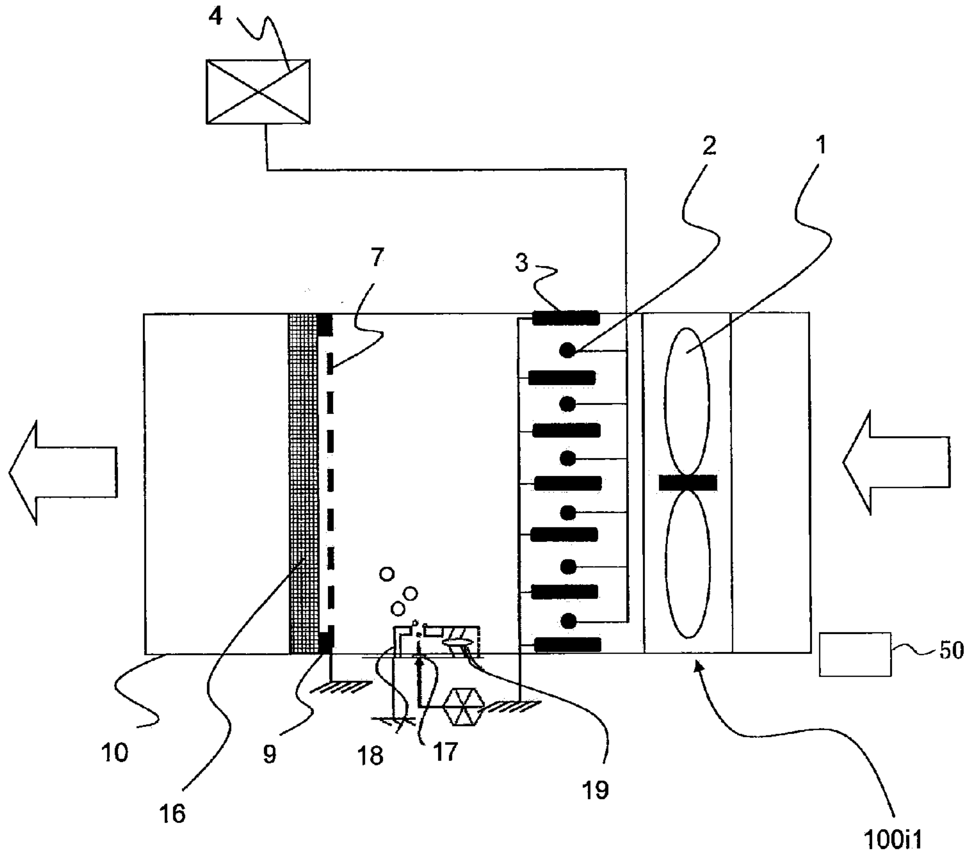
FIG. 20 is a sectional view illustrating a longitudinal section of a schematic configuration of an apparatus for capture and inactivation of microbes and viruses according to Embodiment 8 of the present invention.
Figure 21:
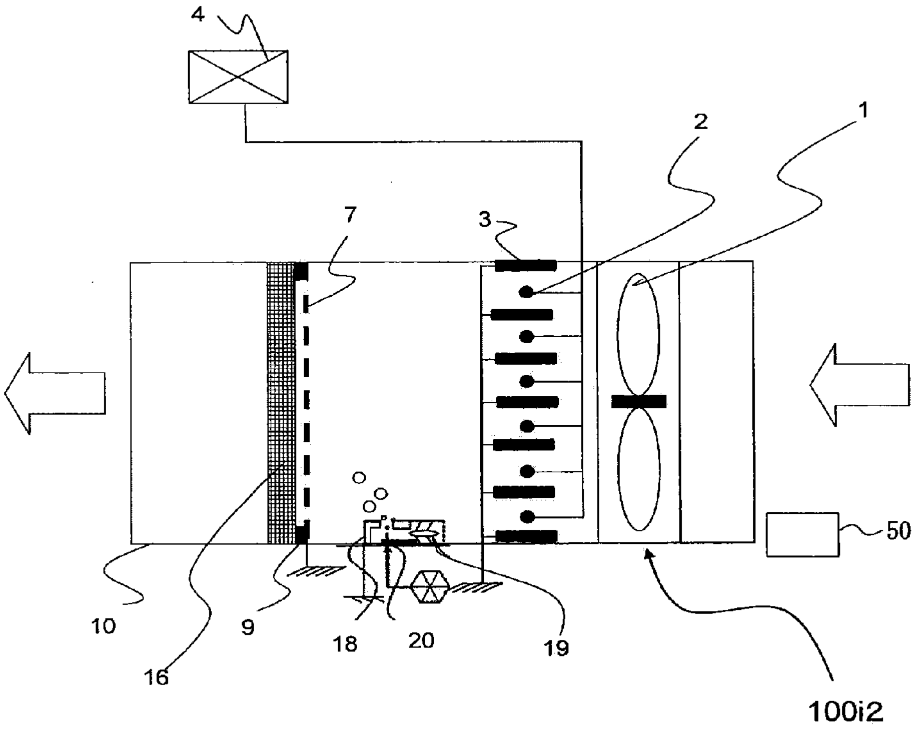
FIG. 21 is a sectional view illustrating a longitudinal section of a schematic configuration of an apparatus for capture and inactivation of microbes and viruses according to a modification of Embodiment 8 of the present invention.

FIG. 20 is a sectional view illustrating a longitudinal section of a schematic configuration of an apparatus (hereinafter, referred to as the "apparatus 100*i*1") for capture and inactivation of microbes and viruses according to Embodiment 8 of the present invention. FIG. 21 is a sectional view illustrating a longitudinal section of a schematic configuration of an apparatus (hereinafter, referred to as the "apparatus 100*i*2") for capture and inactivation of microbes and viruses according to a modification of Embodiment 8 of the present invention. The configurations and operations of the apparatuses 100*i*1 and 100*i*2 will be described with reference to FIGS. 20 and 21. The difference between Embodiment 8 and Embodiments 1 to 7 will be mainly described. The same components as those in Embodiments 1 to 7 are designated by the same reference numerals. Furthermore, the flow of air is indicated by arrows in FIGS. 20 and 21.

In the configuration in each of Embodiments 1 to 7, the charging-unit high-voltage electrode (the charging-unit high-voltage electrode 2, the charging-unit high-voltage electrode 12) is disposed on the windward side and the charging-unit ground electrode (the charging-unit ground electrode 3, the charging-unit ground electrode 11) is disposed on the leeward side to charge microorganisms suspended in the air, and the microorganisms are inactivated with ozone generated by the charging-unit high-voltage electrode 2 and the charging-unit ground electrode 3 during inactivation. According to Embodiment 8, as illustrated in FIG. 20, an ion generating unit including a discharge electrode (first high-voltage application electrode) 17, a ground electrode 18, a fan 19, and the high voltage power supply 8 is disposed between the charging unit (including the charging-unit high-voltage electrode 2 and the charging-unit ground electrode 3) and the capturing/inactivating unit (including the electrostatic filter 16 and the capturing/inactivating-unit ground electrode 7) such that the ion generating unit is placed on, for example, an inner wall of the air path housing 10 to charge airborne microorganisms with ions generated.

As illustrated in FIG. 21, the apparatus 100*i*2 is configured such that a charged-mist generating unit including a charged-mist spray electrode 20, the ground electrode 18, the fan 19, and the high voltage power supply 8 is disposed on, for example, an inner wall of the air path housing 10. Airborne microorganisms may be charged with charged mist.

The configurations of the apparatuses 100*i*1 and 100*i*2 achieve rapid inactivation of microbes and viruses, though the number of components is increased.

Embodiment 9

Figure 22:
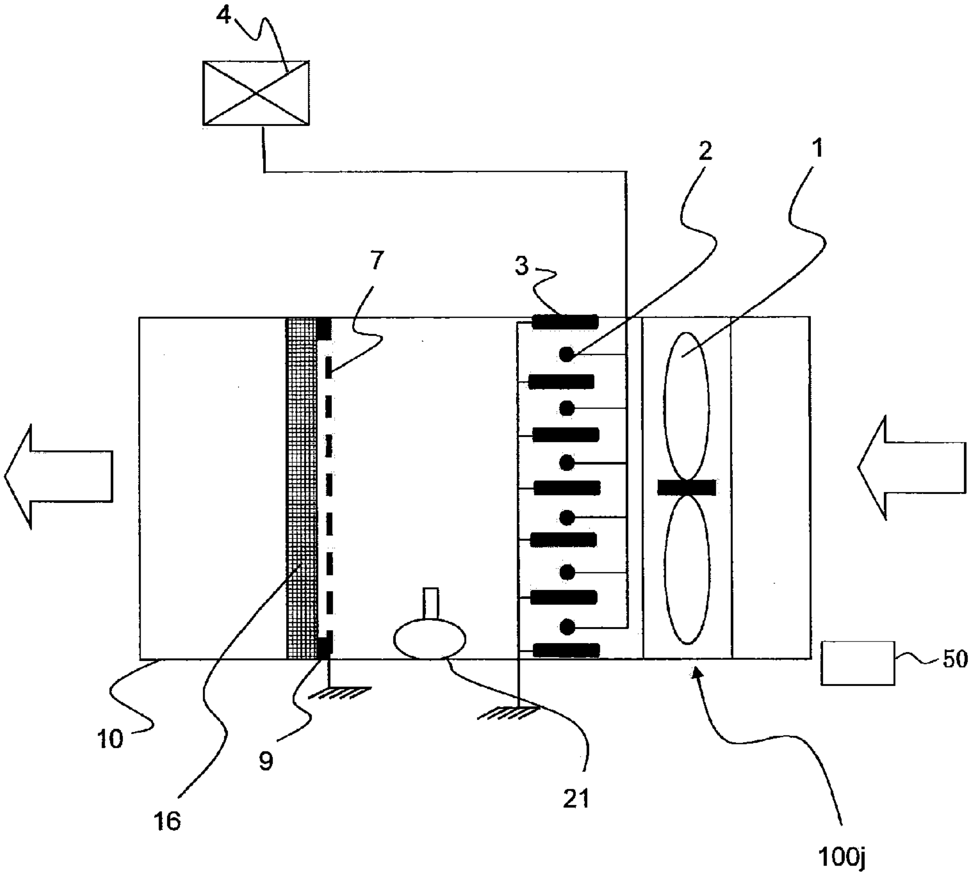
FIG. 22 is a sectional view illustrating a longitudinal section of a schematic configuration of an apparatus for capture and inactivation of microbes and viruses according to Embodiment 9 of the present invention.

FIG. 22 is a sectional view illustrating a longitudinal section of a schematic configuration of an apparatus (hereinafter, referred to as the "apparatus 100*j*") for capture and inactivation of microbes and viruses according to Embodiment 9 of the present invention. The configuration and operation of the apparatus 100*j* will be described with reference to FIG. 22. The difference between Embodiment 9 and Embodiments 1 to 8 will be mainly described. The same components as those in Embodiments 1 to 8 are designated by the same reference numerals. The flow of air is indicated by arrows in FIG. 22.

In the configuration in each of Embodiments 1 to 7, the charging-unit high-voltage electrode (the charging-unit high-voltage electrode 2, the charging-unit high-voltage electrode 12) is disposed on the windward side and the charging-unit ground electrode (the charging-unit ground electrode 3, the charging-unit ground electrode 11) is disposed on the leeward side to charge microorganisms suspended in the air, and the microorganisms are inactivated with ozone generated by the charging-unit high-voltage electrode 2 and the charging-unit ground electrode 3 during inactivation. According to Embodiment 9, as illustrated in FIG. 22, a humidifier 21 is disposed between the charging unit (including the charging-unit high-voltage electrode 2 and the charging-unit ground electrode 3) and the capturing-inactivating unit (including the electrostatic filter 16 and the capturing/inactivating-unit ground electrode 7) to mix airborne microorganisms, charged by the charging unit, with water supplied from the humidifier 21.

This configuration offers the advantages described in Embodiments 1 to 8 and further enables charged airborne microorganisms to be supplied with moisture. Advantageously, the advantage of capturing airborne microorganisms through the capturing unit can be further increased.

Figure 23:
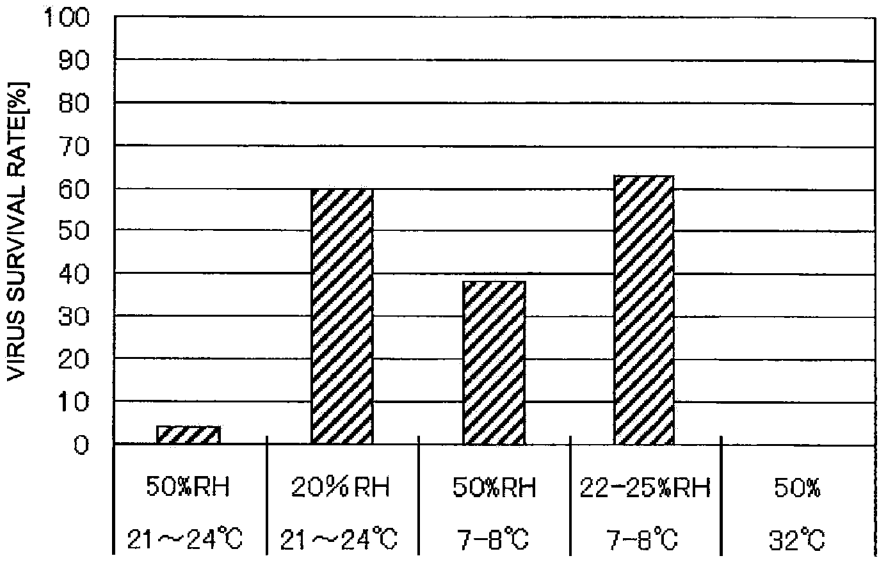
FIG. 23 is a graph of the effect of temperature and humidity on influenza virus inactivation.

FIG. 23 illustrates a change in influenza virus survival rate with varying temperature and humidity after being left for six hours as it was. FIG. 23 demonstrates that the activity of the virus increased under low temperature and low humidity conditions, whereas it decreased under high temperature and high humidity conditions. Furthermore, it is known that the activity of microbes increases under relatively high temperature conditions and it decreases under low humidity conditions, because microbes are sensitive to drying. Accordingly, water supply during virus inactivation leads to more effective virus inactivation.

While the apparatuses and methods for capture and inactivation of microbes and viruses according to the present invention have been described with respect to Embodiments 1 to 9, the features of Embodiments 1 to 9 may be properly combined to provide an apparatus and method for capture and inactivation of microbes and viruses.

REFERENCE SIGNS LIST

1 air-sending device 2 charging-unit high-voltage electrode 3 charging-unit ground electrode 4 high voltage power supply 4*a* high voltage power supply 5 capturing/inactivating-unit high-voltage electrode 6 hydrophilic filter 7 capturing/inactivating-unit ground electrode 8 high voltage power supply 9 bushing 10 air path housing 11 charging-unit ground electrode 12 charging-unit high-voltage electrode 13 safety guard 14 voltage regulator 14*a* voltage regulator 14*b* voltage regulator 15 honeycomb 15*a* hydrophilic honeycomb 15*b* catalyst-coated honeycomb electrostatic filter 18 ground electrode 19 fan 20 charged-mist spray electrode 21 humidifier 50 controller 100 apparatus 100*a* apparatus 100*b* apparatus 100*c* apparatus 100*d* apparatus 100*e* apparatus 100*e* apparatus 100*f* apparatus 100*g*1 apparatus 100*g*2 apparatus 100*h* apparatus 100*i*1 apparatus 100*i*2 apparatus 100*j* apparatus a space

The invention claimed is:

1. A method for capture and inactivation of microbes and viruses, the method comprising:
- a step of introducing airborne microorganisms into an air path housing;
- a charging step of charging the airborne microorganisms introduced in the air path housing;
- a filter capturing step of capturing the charged airborne microorganisms with a hydrophilic filter which has been polarized; and
- a step of inactivating the airborne microorganisms captured by the hydrophilic filter with plasma,
- wherein the step of inactivating the airborne microorganisms captured by the hydrophilic filter with plasma is started after the charging step and the filter capturing step.

2. The method for capture and inactivation of microbes and viruses of claim 1, wherein the steps are successively performed.

3. The method for capture and inactivation of microbes and viruses of claim 1, wherein there are provided
- an air path housing,
- a first high-voltage application electrode to be supplied with a voltage to charge airborne microorganisms introduced in the air path housing,
- a first counter electrode disposed so as to face the first high-voltage application electrode,
- the hydrophilic filter sandwiched between a second high-voltage application electrode and a second counter electrode, the hydrophilic filter being configured to capture the airborne microorganisms charged by the first high-voltage application electrode, and
- a single high voltage power supply to supply a voltage to the first high-voltage application electrode and the second high-voltage application electrode.

4. The method for capture and inactivation of microbes and viruses of claim 3, wherein the hydrophilic filter is coated with at least one of a hydrophilic catalyst, an absorbent, and a deodorant catalyst.

5. The method for capture and inactivation of microbes and viruses of claim 1, wherein there are provided
- an air path housing,
- a first high-voltage application electrode to be supplied with a voltage to charge airborne microorganisms introduced in the air path housing,
- a first counter electrode disposed so as to face the first high-voltage application electrode,
- the hydrophilic filter charged in advance to capture the airborne microorganisms charged by the first high-voltage application electrode, and
- a ground electrode disposed in a more windward side than the hydrophilic filter.

6. The method for capture and inactivation of microbes and viruses of claim 5, wherein the hydrophilic filter is coated with at least one of a hydrophilic catalyst, an absorbent, and a deodorant catalyst.

7. A method for capture and inactivation of microbes and viruses, the method comprising:
- a step of introducing airborne microorganisms into an air path housing;
- a step of producing a discharge between a first high-voltage application electrode and a first counter electrode disposed so as to face the first high-voltage application electrode in the air path housing to charge the airborne microorganisms introduced in the air path housing;
- a capturing step of capturing the charged airborne microorganisms using a hydrophilic filter charged in advance; and
- a step of inactivating the airborne microorganisms after the capturing step and sending air,
- wherein the steps are successively performed.

8. An apparatus for capture and inactivation of microbes and viruses, the apparatus comprising:
- an air path housing;
- a first high-voltage application electrode to be supplied with a voltage to charge airborne microorganisms introduced in the air path housing;
- a first counter electrode disposed so as to face the first high-voltage application electrode;
- a filter to capture the airborne microorganisms charged by the first high-voltage application electrode;
- a second high-voltage application electrode to be supplied with a voltage to polarize the filter and inactivate the airborne microorganisms captured by the filter;
- a second counter electrode disposed so as to face the second high-voltage application electrode; and
- a power supply to supply a voltage to each of the first high-voltage application electrode and the second high-voltage application electrode,
- wherein the filter has a hydrophilic surface, and
- wherein the filter is sandwiched between the second high-voltage application electrode and the second counter electrode so as to be insulated from the electrodes.

9. The apparatus for capture and inactivation of microbes and viruses of claim 8, wherein a voltage supplied to at least one of the first high-voltage application electrode and the second high-voltage application electrode is adjustable.

10. The apparatus for capture and inactivation of microbes and viruses of claim 8, wherein a voltage supplied to at least one of the first high-voltage application electrode and the second high-voltage application electrode is allowed to be supplied from a same power supply.

* * * * *